US012485034B2

(12) United States Patent
O'Grady et al.

(10) Patent No.: US 12,485,034 B2
(45) Date of Patent: Dec. 2, 2025

(54) NUTRIENT RECYCLING DEVICE

(71) Applicant: The Insides Company Limited, Auckland (NZ)

(72) Inventors: Gregory Brian O'Grady, Auckland (NZ); John Bilkey Davidson, Auckland (NZ); Robert Bruce Davidson, Auckland (NZ); Ian Peter Bissett, Auckland (NZ); Mackenzie Liam Greenslade, Auckland (NZ)

(73) Assignee: The Insides Company Limited, Auckland (NZ)

( * ) Notice: Subject to any disclaimer, the term of this patent is extended or adjusted under 35 U.S.C. 154(b) by 4 days.

(21) Appl. No.: 18/539,733

(22) Filed: Dec. 14, 2023

(65) Prior Publication Data

US 2024/0108493 A1 Apr. 4, 2024

Related U.S. Application Data

(63) Continuation of application No. 16/754,476, filed as application No. PCT/IB2018/057792 on Oct. 9, 2018, now Pat. No. 11,844,717.

(51) Int. Cl.
*A61F 5/44* (2006.01)
*A61F 5/443* (2006.01)
(Continued)

(52) U.S. Cl.
CPC .......... *A61F 5/4405* (2013.01); *A61F 5/4407* (2013.01); *A61F 5/443* (2013.01);
(Continued)

(58) Field of Classification Search
CPC ....... A61J 15/0069; A61J 15/0076; A61J 1/10
See application file for complete search history.

(56) References Cited

U.S. PATENT DOCUMENTS 1,217,567 A 2/1917 Clare
2,524,750 A 10/1950 Bellinger
(Continued)

FOREIGN PATENT DOCUMENTS

CN 204233499 U 4/2015
CN 106310407 A 1/2017
(Continued)

OTHER PUBLICATIONS

K. Al-Harbi et al., "Mucous Fistula Refeeding in Neonates With Short Bowel Syndrome," Journal of Pediatric Surgery, vol. 34, No. 7 (Jul.), 1999, pp. 1100-1103.
(Continued)

*Primary Examiner* — Rebecca E Eisenberg
*Assistant Examiner* — Ted Yang
(74) *Attorney, Agent, or Firm* — McCarter & English, LLP

(57) ABSTRACT

A nutrient recycling device is provided that is configured to collect digestive contents from a first opening of a gastrointestinal (GI) tract and recycle and/or return the digestive contents to a second location in a patient's gastrointestinal tract. The device and associated method may find application in patients with a number of complaints, such as short bowel syndrome and/or prior to stoma reversal surgery. The device comprises a bag adapted to receive the digestive contents from a first GI opening, and a pump incorporated with the bag adapted to pump the digestive contents to a second GI location. The pump includes an inlet in fluid communication with the interior of the bag, and an outlet connected to an outlet conduit adapted to provide a flow pathway for the digestive content to flow from the pump to second GI location.

28 Claims, 12 Drawing Sheets

(51) Int. Cl.
*A61F 5/445* (2006.01)
*A61J 15/00* (2006.01)

(52) U.S. Cl.
CPC ........... *A61F 5/445* (2013.01); *A61J 15/0076* (2015.05); *A61J 15/0092* (2013.01)

(56) References Cited

U.S. PATENT DOCUMENTS

| | | | | | |
|---|---|---|---|---|---|
| 3,042,041 | A | | 7/1962 | Jascalevich | |
| 3,298,610 | A | | 1/1967 | Hirano | |
| 3,937,224 | A | | 2/1976 | Uecker | |
| 4,356,824 | A | | 11/1982 | Vazquez | |
| 4,983,102 | A | | 1/1991 | Swain | |
| 6,093,869 | A | | 7/2000 | Roe et al. | |
| 6,447,472 | B1 | | 9/2002 | Moss | |
| 6,840,923 | B1 | | 1/2005 | Lapcevic | |
| 7,294,120 | B1 | | 11/2007 | Eidsen et al. | |
| 7,648,479 | B2 | | 1/2010 | Solovay | |
| 7,666,171 | B2 | | 2/2010 | Mombrinie et al. | |
| 8,808,221 | B2 | | 8/2014 | Kamen et al. | |
| 9,452,081 | B2 | | 9/2016 | Forsell | |
| 10,028,893 | B2 | | 7/2018 | Kane et al. | |
| 10,136,979 | B2 | | 11/2018 | Forsell | |
| 10,166,139 | B2 | | 1/2019 | Logier et al. | |
| 10,568,998 | B2 | | 2/2020 | Akkerman et al. | |
| 2004/0006320 | A1 | | 1/2004 | Buglino | |
| 2006/0264829 | A1 | * | 11/2006 | Donaldson | A61M 5/142 604/890.1 |
| 2006/0270970 | A1 | | 11/2006 | Moss | |
| 2008/0195047 | A1 | * | 8/2008 | Price | A61J 15/0076 604/151 |
| 2008/0319391 | A1 | * | 12/2008 | Jackson | A61J 15/0069 604/404 |
| 2012/0130341 | A1 | | 5/2012 | Whitley | |
| 2015/0225131 | A1 | * | 8/2015 | Gewirtz | A61J 15/0069 53/469 |
| 2015/0351954 | A1 | * | 12/2015 | Logier | A61F 5/445 604/335 |
| 2016/0022544 | A1 | * | 1/2016 | Turner | A61M 39/1011 604/533 |
| 2018/0265238 | A1 | * | 9/2018 | Wilson | A61J 9/005 |
| 2018/0353318 | A1 | | 12/2018 | Logier et al. | |
| 2020/0222281 | A1 | * | 7/2020 | Ding | A61J 1/2024 |
| 2021/0299353 | A1 | * | 9/2021 | Mannu | A61M 5/1723 |
| 2022/0023148 | A1 | * | 1/2022 | Lema Martinez | A61J 1/2024 |

FOREIGN PATENT DOCUMENTS

| | | | |
|---|---|---|---|
| CN | 106798962 | A | 6/2017 |
| CN | 107080612 | A | 8/2017 |
| GB | 2539890 | A | 1/2017 |

OTHER PUBLICATIONS

E. Levy et al., "High-Output external fistulae of the small bowel: management with continuous enteral nutrition," Br. J. Surg., 1989, vol. 76, Jul., pp. 676-679.

K. Schafer et al., "Continuous extracorporeal stool-transport system: a new and economical procedure for transito short-bowel syndrome in prematures and newborns," Pediatr. Surg. Int., (1997) 12, pp. 73-75.

* cited by examiner

FIGURE 3A
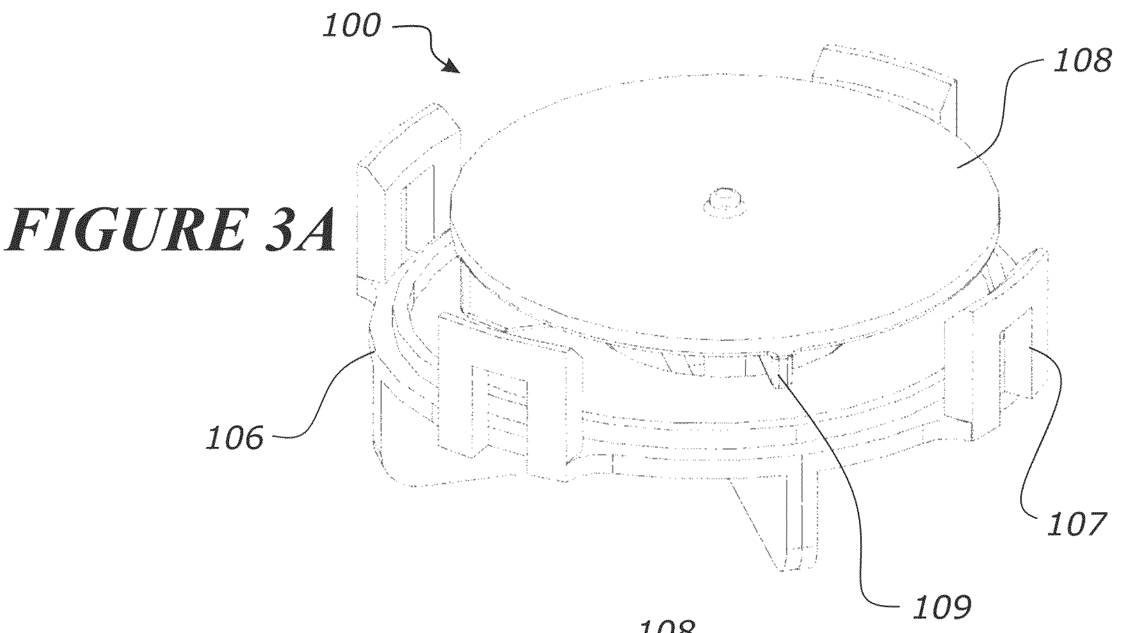
FIGURE 3B
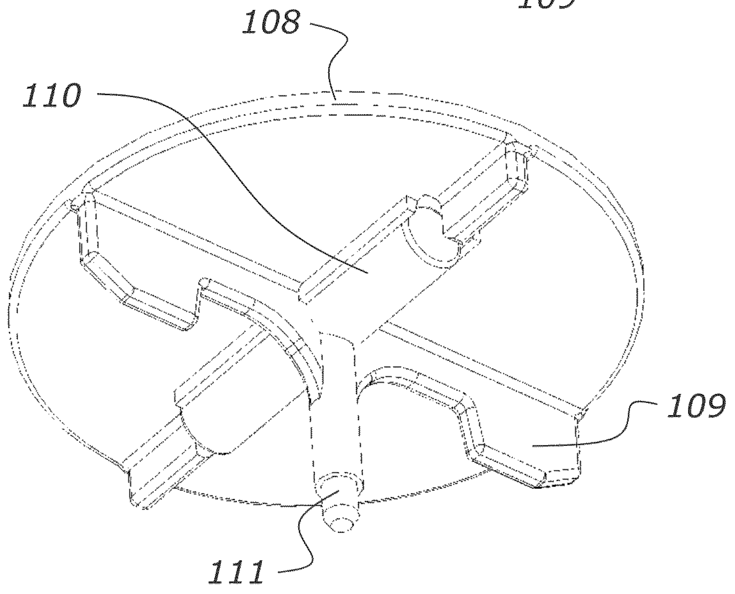
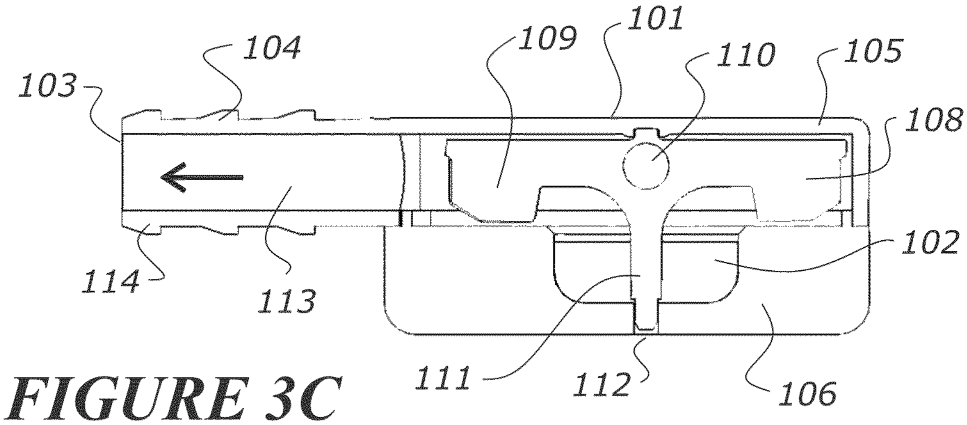
FIGURE 3C

NUTRIENT RECYCLING DEVICE

CROSS-REFERENCE TO RELATED APPLICATIONS

This application claims benefit under 35 U.S.C. § 120 to co-pending U.S. application Ser. No. 16,754,476, filed Apr. 8, 2020, which is a U.S. national phase entry of PCT application no. PCT/IB2018/057792 filed Oct. 9, 2018, claiming priority under 35 U.S.C. § 119(a)-(d) to New Zealand application no. 737381, filed Nov. 15, 2017, and New Zealand application no. 736237, filed Oct. 9, 2017, all of which are hereby incorporated by reference in their entirety as part of the present disclosure.

FIELD OF THE INVENTION

The present invention relates to a nutrient recycling device. More particularly, but not exclusively, it relates to a nutrient recycling device for gastrointestinal stomas and fistulas.

BACKGROUND

Colorectal cancer is a cancer, which develops from the colon or rectum and is currently the third most prevalent cancer worldwide. Ileostomies remain a cornerstone of colorectal cancer management, particularly for rectal cancer management. Ileostomy involves dividing the ileum (the distal small bowel) and bringing one or both ends onto the skin of a patient so that digestive contents can flow into a stoma bag. Traditionally, the digestive contents bypass the colon and are collected in the stoma bag and then emptied manually.

Loop ileostomy is a common type of ileostomy that is intended to temporarily divert digestive contents, while the gastrointestinal tract distal to the ileum heals after colorectal surgery. It is usually intended that the loop ileostomy will be reversed by re-connecting the divided ends of the bowel back together, once healing has occurred. A radiological test is usually performed before the reversal surgery, to confirm that healing has occurred and that the bowel is not leaking. Usually a patient requires at least 1-2 weeks for their gastrointestinal tract distal to the ileum to heal sufficiently to perform a radiological leak test and consider reversal surgery.

After a leak test, some patients may have an "early reversal" of their ileostomy, performed within 1-2 weeks after surgery.

However, it is more usual for ileostomy reversal surgery to occur around 6-12 weeks after surgery. It is generally not considered to be safe to perform the reversal surgery between 2-6 weeks after surgery, because of the presence of internal adhesions that increase surgical risk. If a patient is having chemotherapy, they may need to retain an ileostomy for many months until the chemotherapy is finished, before surgery can be safely performed.

As digestive contents are evacuated from the patient's body, patients may suffer from fluid, electrolyte and nutrient losses as ileostomy bypasses the colon, which resorbs water, electrolytes and certain nutrients. As a result, patients may experience dehydration and subsequent renal injury, and may need to be readmitted to hospital for management with intravenous fluid replacement. Some patients have "high output" ileostomies, being at increased risk of dehydration and renal injury, and may therefore need to be additionally managed with medications that slow gut transit, and with oral rehydration solutions that may be poorly tolerated. Stoma patients often use a lot of hospital resources due to the additional management required, and the related readmissions due to stoma-related dehydration.

Ileostomy patients having chemotherapy, may also suffer excessive stoma output during chemotherapy, which leads to dose reductions and suboptimal therapy. Leaving the colon without any internal nutrients for an extended duration may also increase the risk of "anterior resection syndrome", which is poor bowel function after rectal cancer surgery. Anterior resection syndrome is associated with a poorer quality of life in colorectal cancer survivors.

When an ileostomy is reversed, patients may experience ileus (slow recovery of gut function), partly due to the poor condition of the gut distal to the ileostomy due to the lack of nutrition. A loop ileostomy also depletes the bacterial microbiome that normally occupies the colon, which contributes to colonic health, and as a result, patients who undergoing reversal surgery may experience *Clostridium difficile* infections. *Clostridium difficile* infections prolong hospital stay, can cause serious illness, and may require additional treatments such as antibiotics, surgery or fecal transplants.

Another group of patients who may require a stoma bag are patients with enterocutaneous fistulas, which is an abnormal connection between the gut and the skin. An enterocutaneous fistula may arise as a complication of surgery, or due to a traumatic injury, or because of another disease process such as inflammatory bowel disease. Some neonates may get enterocutaneous fistulas or stomas because of a disease called necrotising enterocolitis, where a segment of gut becomes necrotic.

A type of stoma bag is usually placed over the enterocutaneous fistula to catch the digestive contents. Patients with fistulas often experience poor nutrition, and may become dependent on supplementary feeding such as parenteral nutrition, which is given through a vein. Parenteral nutrition is usually an expensive and risky treatment due to the possibilities of line infections and liver damage.

Furthermore, patients generally dislike having to wear and manage a stoma bag and the associated waste contents. Patients may also need to wake overnight to empty their ileostomies, disrupting sleep patterns. It may be desirable to make waste management of the stoma bag easier for patients, carers and medical practitioners.

Short bowel syndrome is another gastrointestinal related disorder that affects many patients. These are patients who have a short functional gut length due to disease or surgery. Patients with short bowel syndrome usually suffer from malnutrition, dehydration and/or diarrhea due to a reduction of functioning gut length.

To increase the intake of nutrients, many patients with short bowel syndrome are dependent on IV therapy or parenteral nutrition. These solutions are often expensive, as it they uses up hospital resources, or when these solutions are administered at home, there is some risk to the patient. It may be desirable to provide an improved or alternative solution to increase the absorption of nutrients in a patient with short bowel syndrome.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

For the purpose of this specification, where method steps are described in sequence, the sequence does not necessarily mean that the steps are to be chronologically ordered in that sequence, unless there is no other logical manner of interpreting the sequence.

It is an object to provide a nutrient recycling device which overcomes or at least partially ameliorates some of the abovementioned disadvantages or which at least provides the public with a useful choice.

SUMMARY

The invention pertains to a nutrient recycling device configured to collect digestive contents from a first gastro-intestinal tract opening and pump the digestive contents to a second gastrointestinal tract opening.

In at least some embodiments, a flexible bag is adapted to receive the digestive contents from the first opening, through a first bag opening, wherein a pump located within the flexible bag or having a pump body incorporated with a wall of the flexible bag is adapted to pump the collected digestive contents to the second gastrointestinal tract opening, the pump comprising a pump inlet in fluid communication with an interior of the flexible bag, and a pump outlet connected to an outlet conduit adapted to provide a flow pathway for the digestive content to flow from the pump to the second gastrointestinal tract opening, and a pump actuator separable from the pump and adapted to be operably coupled to the pump.

In at least some embodiments, the first bag opening is configured to be positioned over the first gastrointestinal tract opening, over the first and second gastrointestinal tract openings, or over the first gastrointestinal tract opening, and a second bag opening is configured to be positioned over the second gastrointestinal tract opening. In at least some embodiments, the bag comprises an attachment portion configured to attach the bag to a patient, and wherein the attachment portion is an adhesive backing. In some such embodiments, the attachment portion is separable from the flexible bag.

In at least some embodiments, the pump is incorporated with the flexible bag by attachment to the inside wall of the flexible bag, to the outside wall of the flexible bag, or includes a pump housing forming at least part of the wall of the flexible bag.

In at least some embodiments the pump is located within the flexible bag, and in some such embodiments, the pump freely floats within the flexible bag supported by the outlet conduit.

In at least some embodiments, the flexible bag further comprises at least one external conduit opening adapted to allow at least one external conduit to communicate between the inside and outside of the flexible bag.

In at least some embodiments, the pump is attached to the bag. In some such embodiments, said attachment is by clips, clasps, buckles, Velcro, zip, slide fastener, snap fasteners and/or magnets. In other such embodiments, the bag comprising a pouch is adapted to locate the pump and the pouch is incorporated into a side wall of the bag.

In at least some embodiments, the outlet conduit comprises a first portion and a second portion, the first portion being located within the bag, and the second portion being located external to the bag. In some such embodiments, the second portion is adapted to be inserted into the gastrointestinal tract through the second gastrointestinal tract opening.

In at least some embodiments, the outlet conduit defines a delivery catheter and includes an output end, and is configured to reintroduce the digestive contents back into a patient. In some such embodiments, the outlet conduit is adapted to be positioned downstream in the gastrointestinal tract from the first opening. In other such embodiments, the outlet conduit is adapted to be positioned upstream from the first opening. In at least some embodiments, the delivery catheter is configured to be in use inserted back upstream through the first gastrointestinal tract opening.

In at least some embodiments, the pump comprises a body, and an impeller driven by a pump actuator. In some such embodiments, the impeller is driven by a magnetic coupling between said pump actuator and said impeller. In other such embodiments, the impeller is driven by a mechanical coupling between said pump actuator and said impeller. In some of the foregoing embodiments, the pump is located inside the bag and the pump actuator is located external to the bag.

In at least some embodiments, the pump defines a syringe configured to push the digestive contents towards the second gastrointestinal tract opening. In some such embodiments, the syringe comprises a plunger external to the bag. In at least some embodiments the pump comprises one or more one-way valves.

In at least some embodiments, the pump comprises a controller configured to: increase or decrease the flow rate of the digestive contents; be operated manually by a patient; operate automatically; operate the pump at set intervals; operate when a predetermined fluid level, bag weight, and/or bacteria level as detected by a sensor is reached; and/or operate the pump in a reverse direction or alternate between a forward direction and a reverse direction, from time to time and/or, when a sensor detects a predetermined condition; to clear blockages.

As used herein, the term "and/or" means "and" or "or", or both, and "(s)" following a noun means the plural and/or singular forms of the noun. The term "comprising" means "consisting at least in part of". When interpreting statements in this specification and claims which include that term, the features, prefaced by that term in each statement, all need to be present but other features can also be present. Related terms such as "comprise" and "comprised" are to be interpreted in the same manner.

Other aspects, objects and advantages of the present invention will become apparent in view of the following detailed description of the embodiments and the accompanying drawings.

BRIEF DESCRIPTION OF THE DRAWINGS

Embodiments will be described below with reference to the drawings. However, those skilled in the art should appreciate that the drawings are only for the purpose of explaining the described embodiments, and therefore do not limit the scope of the invention or the claims herein. In addition, unless otherwise indicated, the drawings are intended only to conceptually represent the described embodiments, and are not necessarily drawn to scale.

FIG. **2*a*** shows a perspective view of the nutrient recycling device.

FIG. **2*b*** shows a perspective view of a flange and guiding portion of the device.

FIG. **3*a*** shows a perspective view of the base and internal components of a pump in the nutrient recycling device.

FIG. 3*b* shows a perspective view of the underside of a movable component in a pump.

FIG. 3*c* shows a cross-section of the pump in FIG. 2.

Figure 4A:
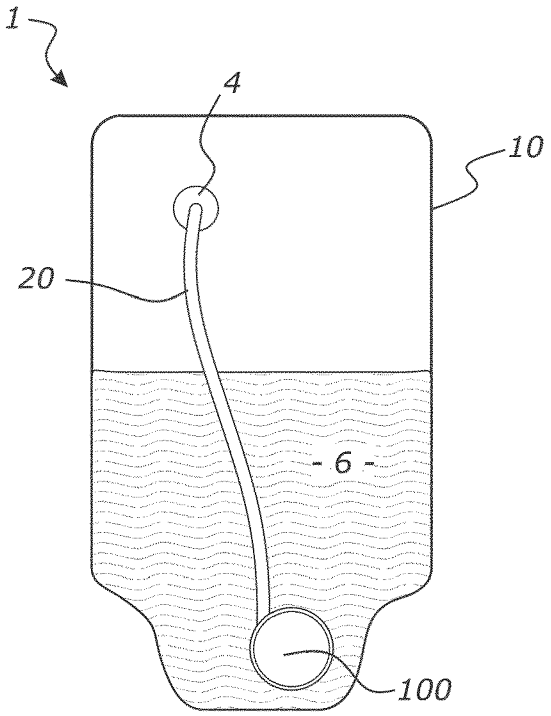

FIG. 4*a* shows a schematic of the nutrient recycling device with a pump located towards the bottom of the bag.

Figure 4B:
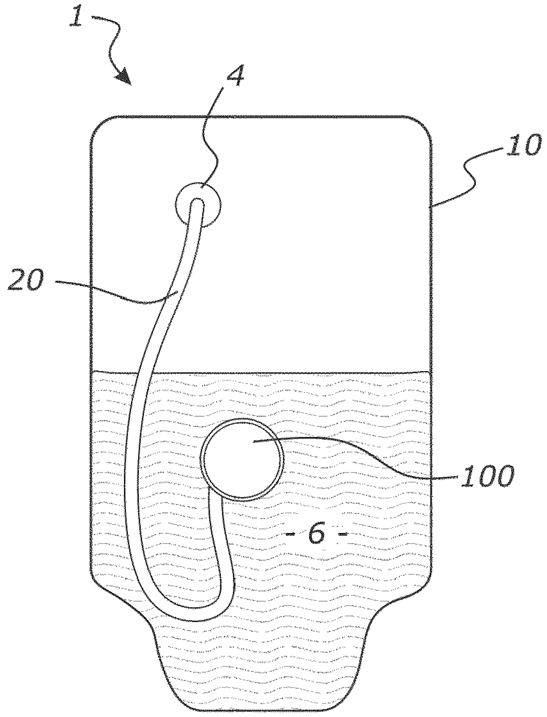

FIG. 4*b* shows a schematic of the nutrient recycling device with a pump located between the top and bottom of the bag.

Figure 4C:
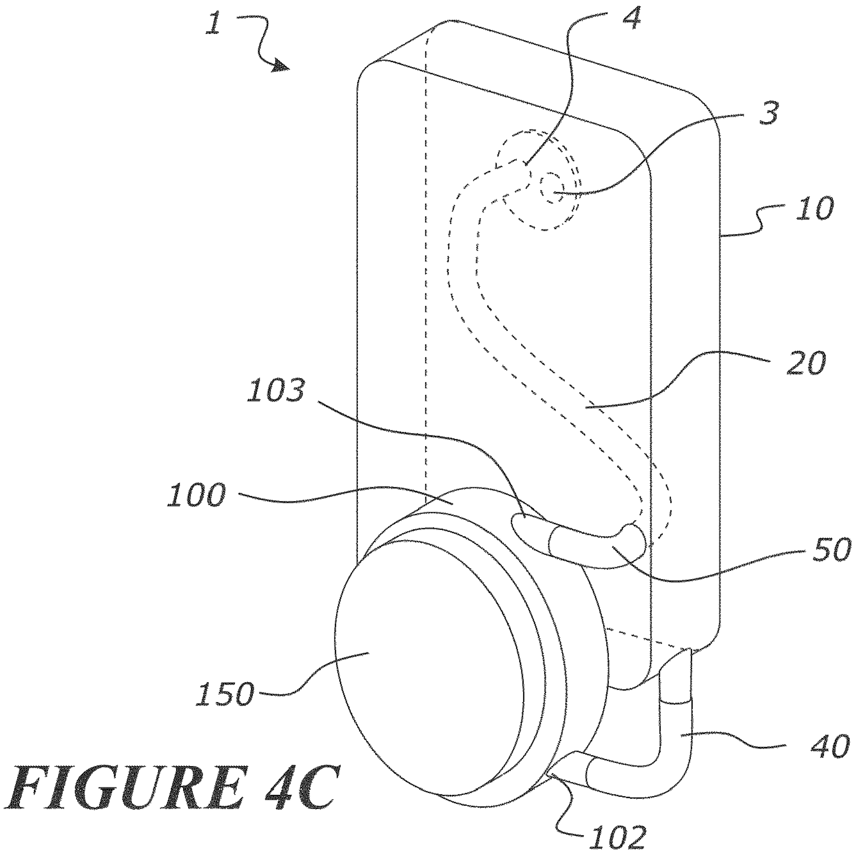

FIG. 4*c* shows a perspective view of a nutrient recycling device with a pump located external to the bag.

Figure 5A:
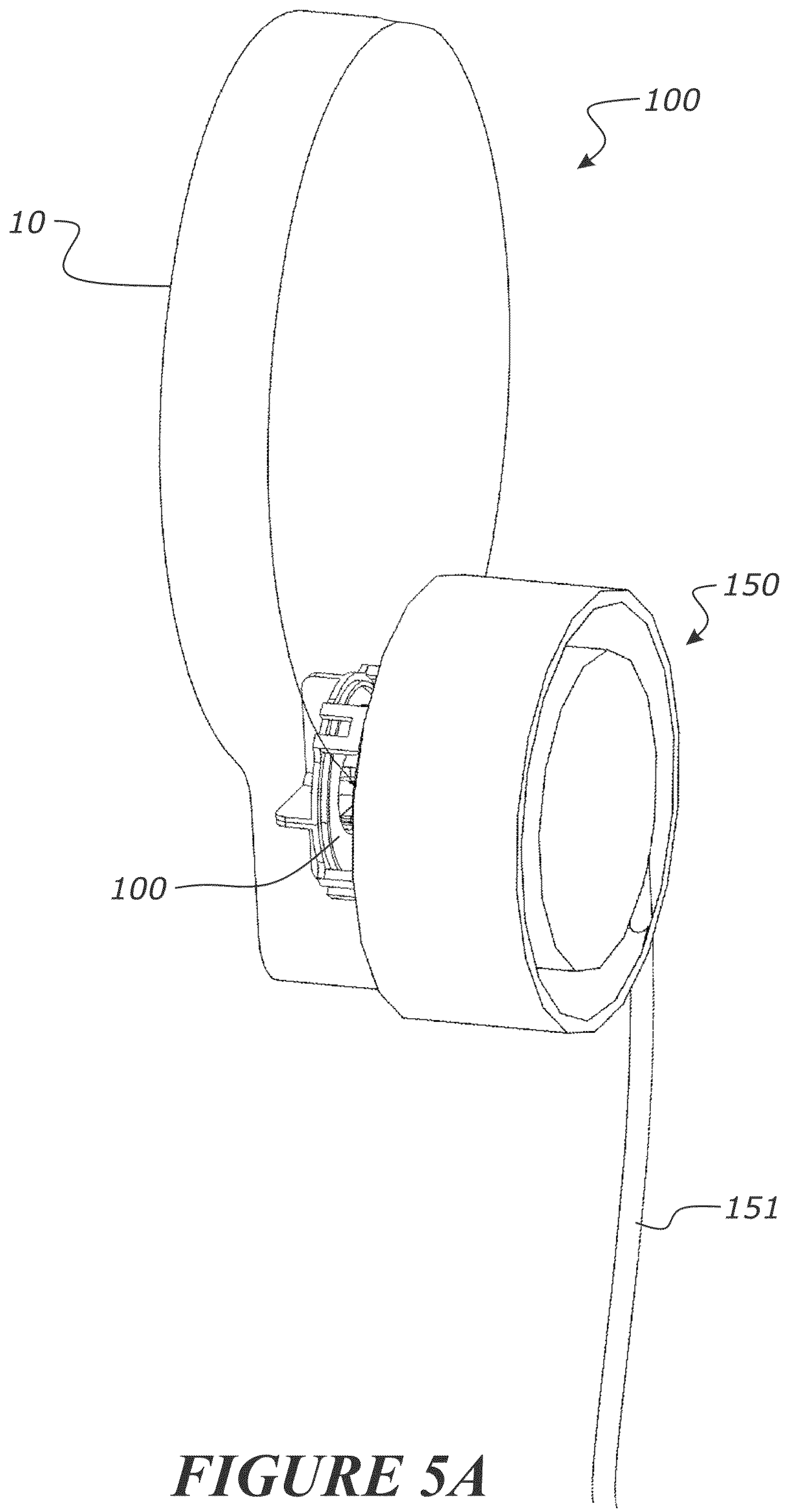

FIG. 5*a* shows a nutrient recycling device with a complementary pump actuator.

Figure 5B:
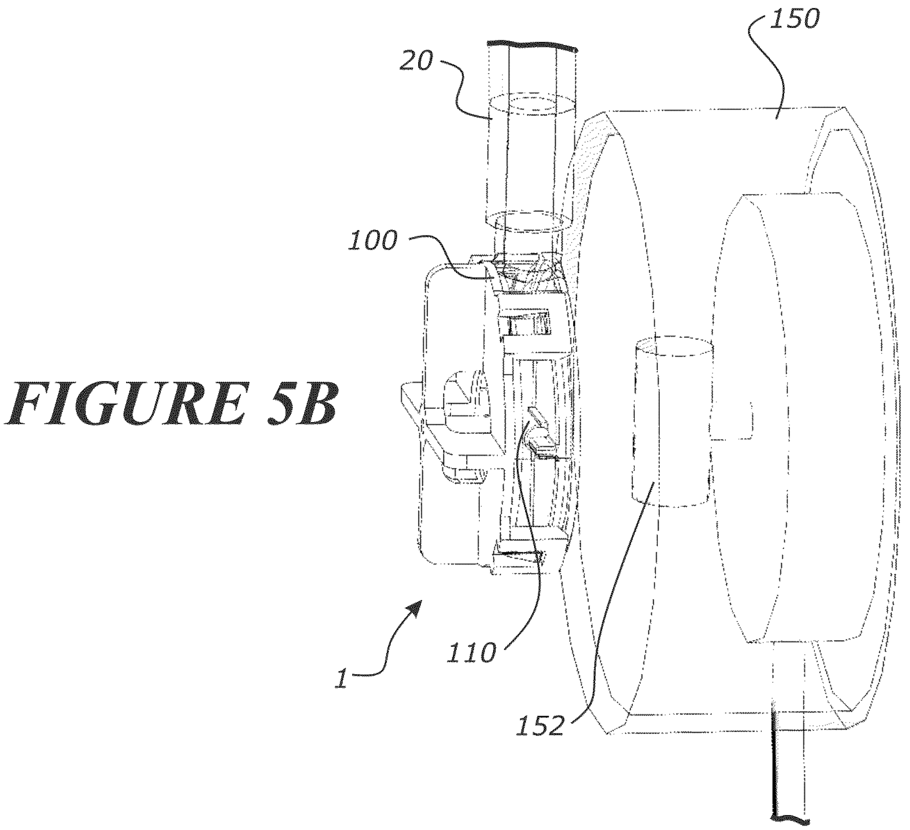

FIG. 5*b* shows a partial perspective view of a nutrient recycling device with a pump actuator with a magnetic driving element.

Figure 5C:
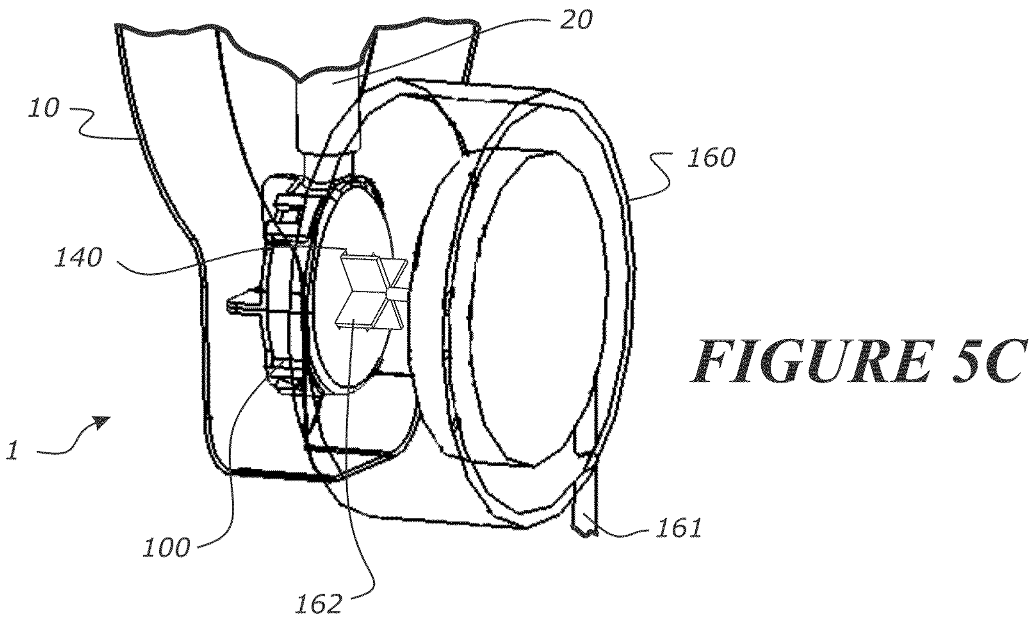

FIG. 5*c* shows a partial perspective view of a nutrient recycling device with a pump actuator with a mechanical driving element.

Figure 6:
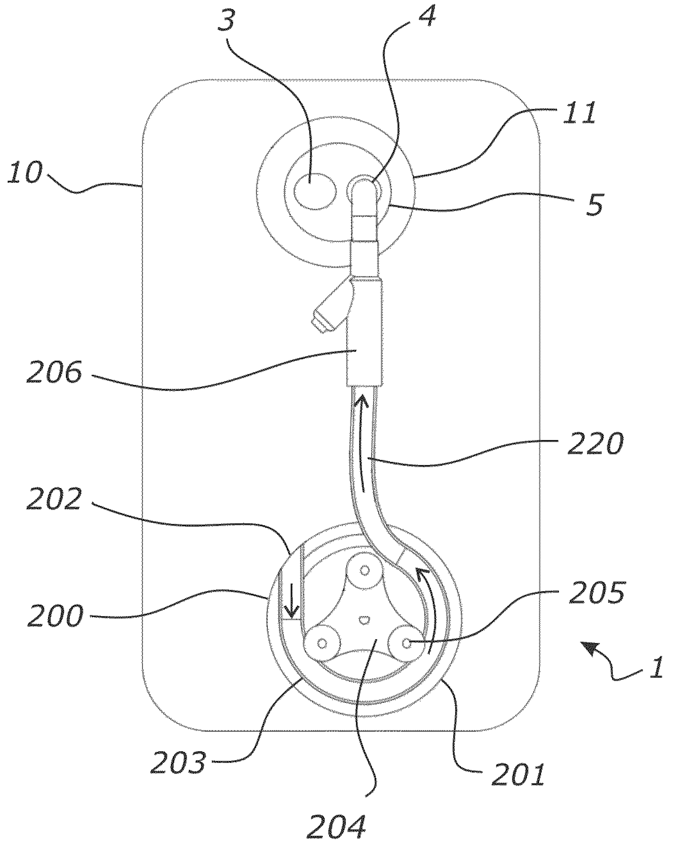

FIG. 6 shows a schematic of a nutrient recycling device with a peristaltic pump.

Figure 7:
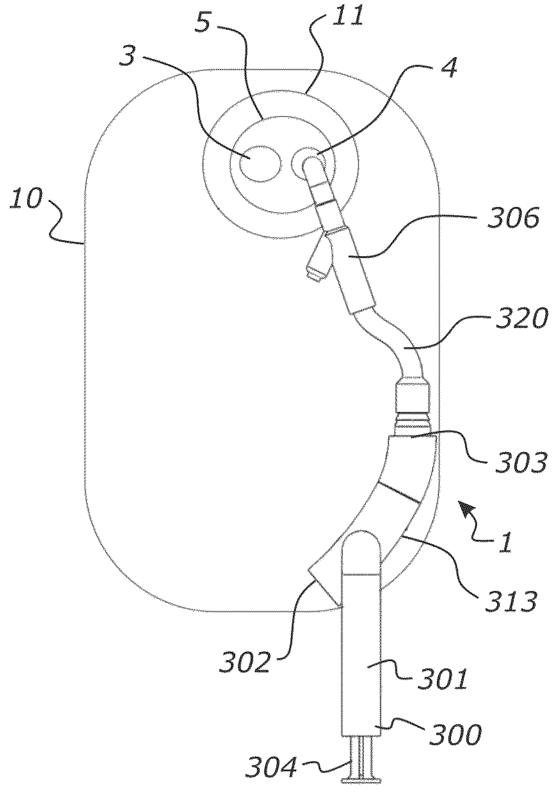

FIG. 7 shows a schematic of a nutrient recycling device with a syringe pump.

Figure 8:
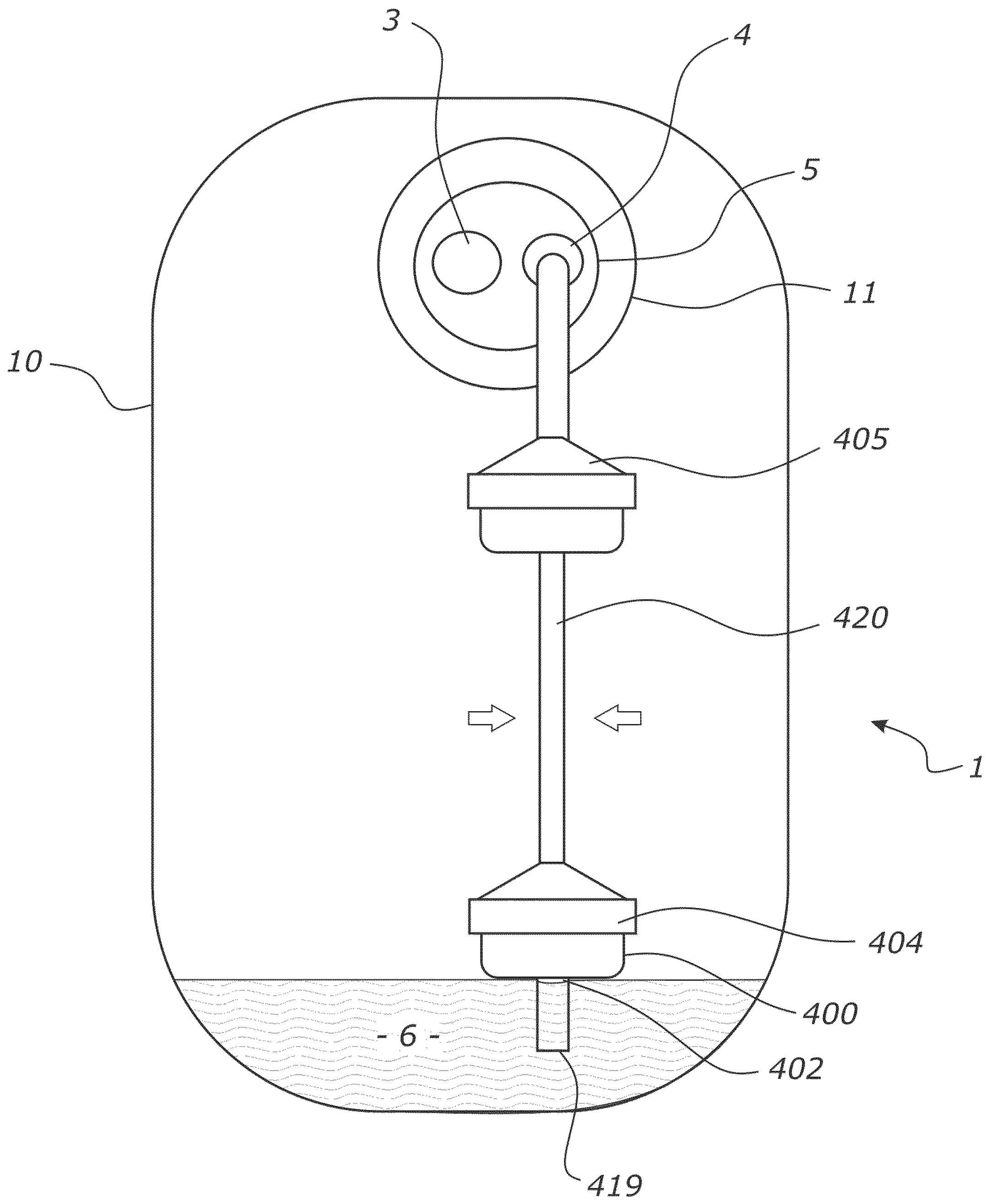

FIG. 8 shows a schematic of a nutrient recycling device with a valve pump.

Figure 9A:
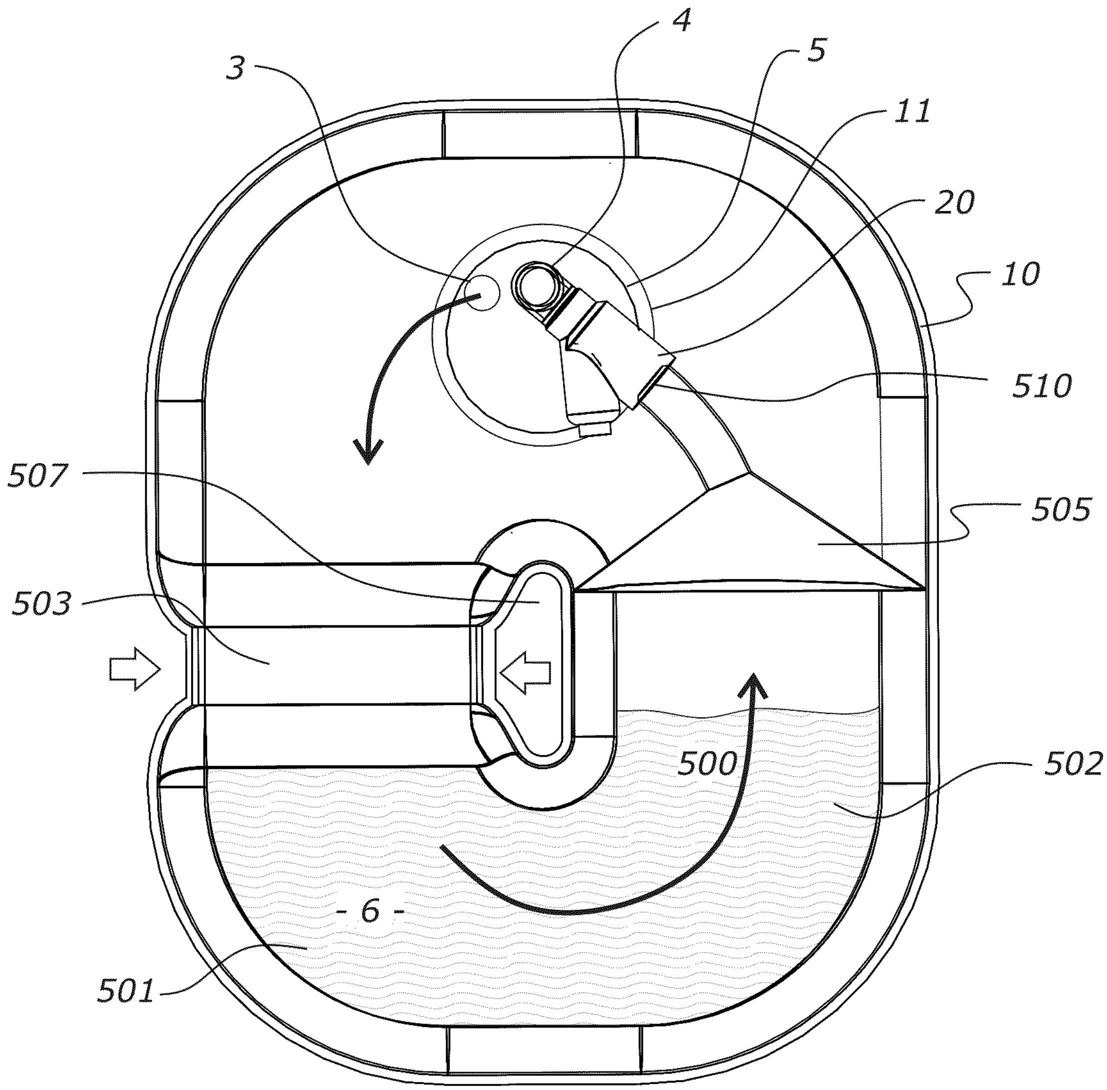

FIG. 9*a* shows a front view of a nutrient recycling device driven by compression.

Figure 9B:
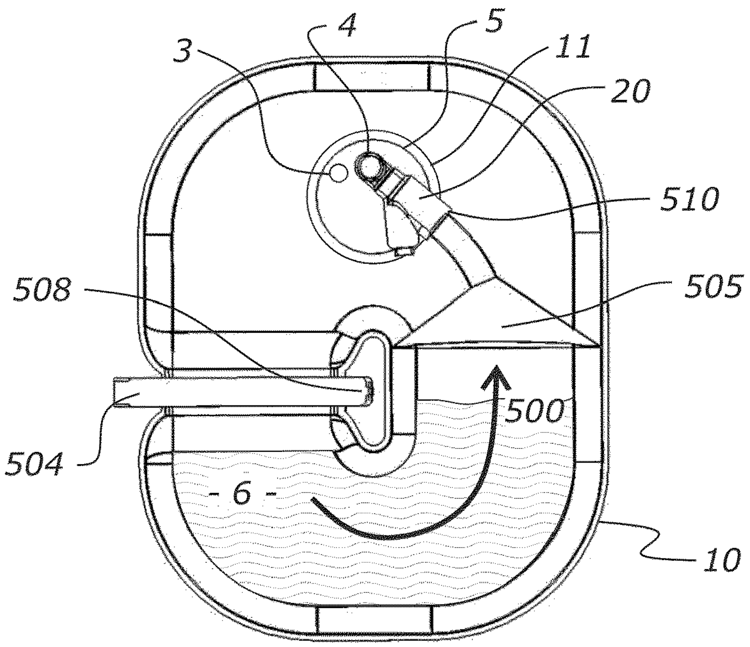

FIG. 9*b* shows a front view of a nutrient recycling device driven by compression including a clip.

Figure 9C:
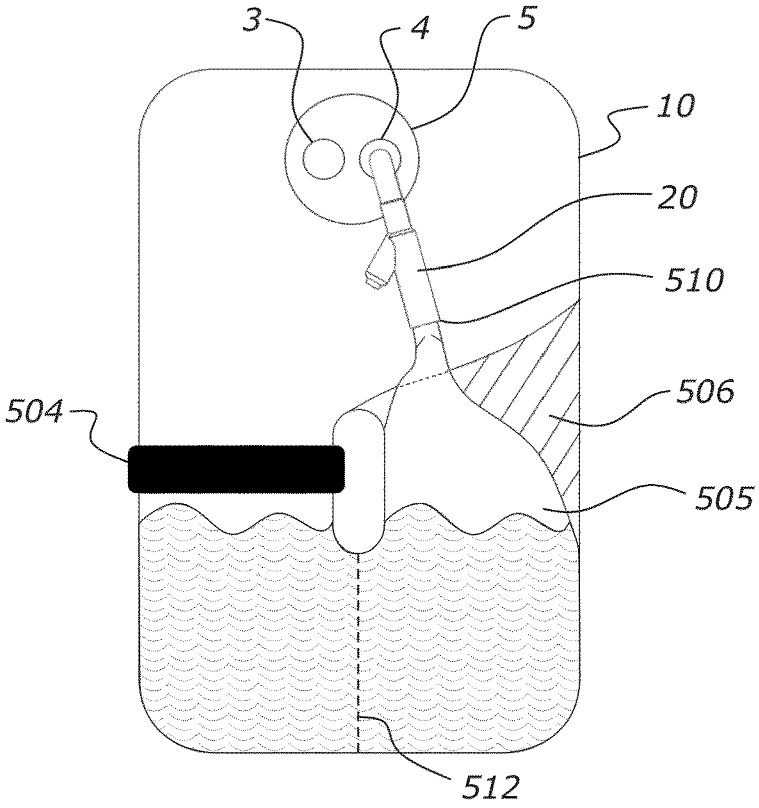

FIG. 9*c* shows a schematic of a nutrient recycling device driven by compression including a sealed section.

Figure 10A:
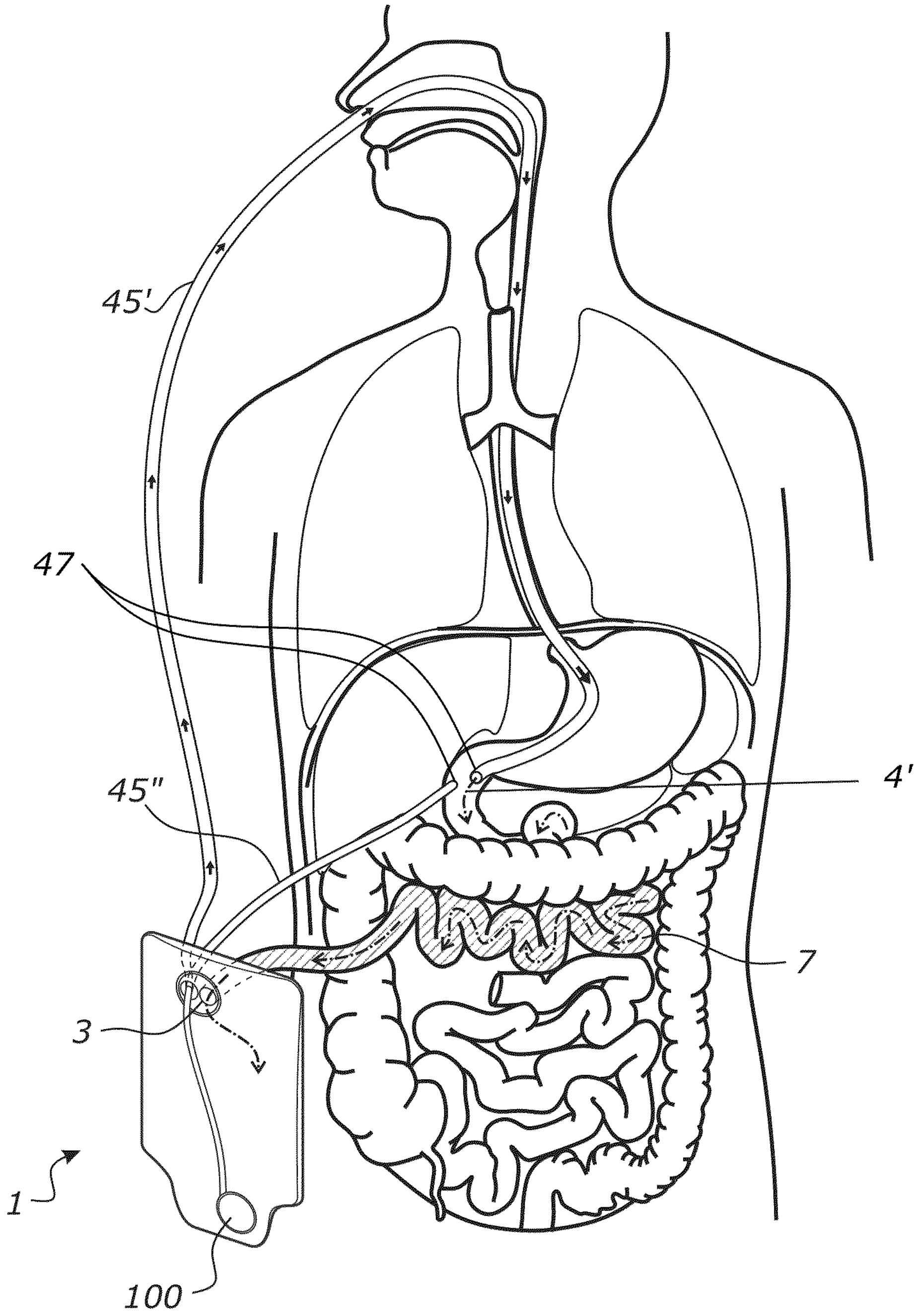

FIG. 10A shows a schematic of a patient and a nutrient recycling device with a delivery tube introduced at different locations.

Figure 10B:
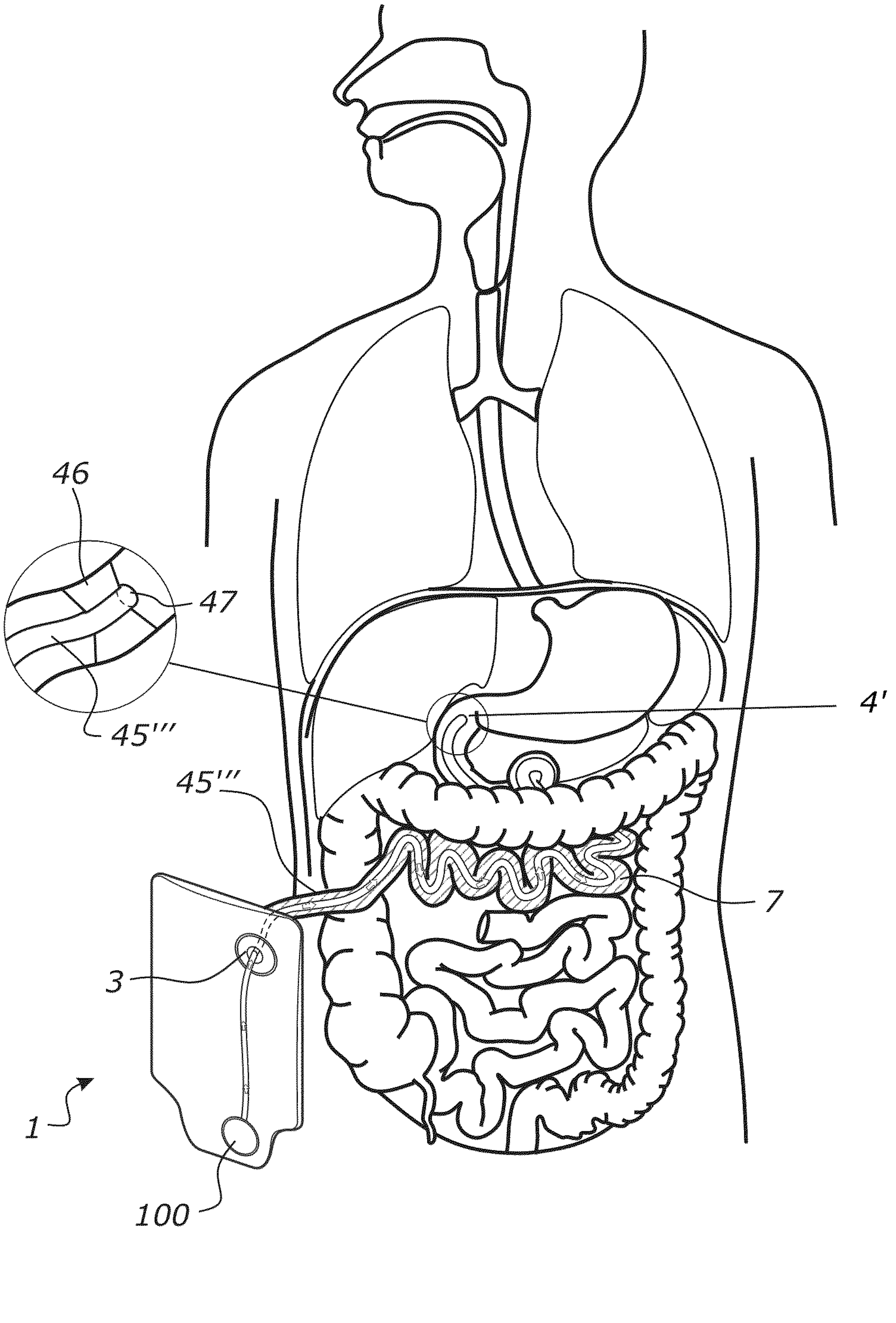

FIG. 10B shows a schematic of a patient and a nutrient recycling device with a delivery tube introduced at another location.

DETAILED DESCRIPTION

Embodiments are described below with reference to the drawings.

With reference to FIGS. 1-10B there is shown a nutrient recycling device 1 configured to collect and recycle digestive contents 6 from the small intestine 2 of a patient.

In at least some embodiments, the nutrient recycling device 1 recycles digestive contents 6 from a first opening 3 of the gastrointestinal tract to a second gastrointestinal tract opening 4. In at least some embodiments, the nutrient recycling device 1 recycles the digestive contents 6 by collecting the digestive contents 6 in the device 1 and pumping the digestive contents 6 towards the second opening 4.

In some configurations, the digestive contents 6 are recycled from a first opening 3 in the gastrointestinal tract to a second downstream opening 4 in the patient. In other configurations, the digestive contents 6 are recycled from a first opening 3 in the gastrointestinal tract to an upstream location in the patients gastrointestinal tract.

In some configurations, the first opening is the proximal opening 3 of the ileum 2 (distal small bowel). In at least some embodiments the second opening is a distal opening 4 of the ileum 2. In this configuration, the digestive contents 6 are recycled downstream from the first opening 3. The device 1 in at least some embodiments limits fluid and nutrient loss from a stoma 5 as digestive contents 6 are recycled back into the digestive tract. In another configuration, the digestive contents 6 are recycled from the first opening 3 of the gastrointestinal tract to an upstream location. In some configurations the upstream location 4' is at or near the jejunum (middle segment of the small intestine, upstream from the ileum) where absorption occurs. In at least some embodiments, the second opening 4 is downstream from the stomach and duodenum.

In at least some embodiments once the digestive contents 6 exits the upstream gastrointestinal tract location 4', the digestive contents 6 flow naturally, such as by smooth muscle contractions, from the upstream location 4', downstream towards the first opening 3 of the gastrointestinal tract. Recycling digestive contents 6 upstream as described in this configuration means that a particular portion of the gastrointestinal tract can be reused as the digestive contents 6 passes along the same multi-circulation gastrointestinal flow path 7, more than once as shown in FIGS. 10A and 10B (shaded-pattern of the gastrointestinal tract). In at least some embodiments, the digestive contents 6 pass through the same flow pathway between the output end 47 and the first opening of the gastrointestinal tract 3 a plurality of times to increase absorption.

In at least some embodiments, the multi-circulation gastrointestinal flow path 7 is defined as part of the gastrointestinal tract between the upstream gastrointestinal tract location 4' to the first gastrointestinal tract opening 3.

It may be possible to reuse the same portion of gastrointestinal tract 7 to increase absorption. This desired segment of the gastrointestinal tract is configured to provide a multi-circulation gastrointestinal flow pathway 7 where the digestive contents 6 flow through the flow pathway more than once. Multi-circulation through the same flow pathway 7 in a desired segment of the gastrointestinal tract may increase the time that nutrients are in contact with the gastrointestinal tract wall, and therefore increase the likelihood of nutrients being absorbed by the patient.

Circulating digestive contents 6 over the same multi-circulation gastrointestinal flow pathway 7 effectively increases the length of gastrointestinal tract which the contents pass over, thus increasing likelihood of nutrient absorption. The desired segment of the gastrointestinal tract may function better than other parts or may have specific absorption characteristics (absorbs particular nutrients). Multi-circulation of digestive contents may be beneficial to patients with nutrient absorption disorders such as short bowel syndrome.

Multi-circulation of digestive contents may also be beneficial for improving electrolyte balance in patients with short-gut syndrome. Electrolytes may be secreted in the upper part of the small bowel before fluid absorption occurs effectively. Recirculating the gut contents back to an upstream location 4' (such as at the jejunum) once the intestinal fluid has reached a physiological concentration of electrolytes may improve the net absorption of fluids and electrolytes. Electrolyte deficits such as sodium and magnesium deficiency may be corrected by this treatment.

Multi-circulation of digestive contents in short-gut syndrome may enable patients to reduce their reliance on intravenous (parenteral) forms of supplementary nutrition. Reducing the reliance on parenteral nutrition may lead to other benefits such as reduced infection risk, improved liver health and reduced cost of care.

The nutrient recycling device 1 in some configurations may also include reducing or eliminating dehydration and renal impairment due to traditional ileostomy, improving chemotherapy patient survival (by allowing fulfilment of chemotherapy regimens), preventing worse colonic function after surgery caused by deprivation of internal nutrients, preservation of the colonic microbiome, and/or reducing the burden of waste content management associated with stoma bags.

It is also anticipated that the device 1 can be used in other medical procedures requiring recycling of waste or other fluid or partially fluid material. The nutrient recycling device 1 may be used to recycle contents from other portions of the gastrointestinal tract.

For example, the nutrient recycling device 1 may be used to manage gastrointestinal fistulas to reduce malnutrition, fluid and electrolyte imbalance. The benefits of the device 1 in small bowel fistulas may be significant, because fistula patients tend to have very high outputs of gut contents, even if they eat nothing at all. This is because the gut makes several liters of fluid each day (gastric juices, pancreatic fluid, bile, saliva, mucosal secretions), which are progressively absorbed along the way toward the colon. Small bowel fistulas, which are not made intentionally, may be located in the mid or upper small bowel, meaning that up to several liters of fluid may be lost per day. These patients are at very high risk of dehydration and renal injury, and their stomas are typically complex to manage, requiring specialist nursing care. Fistula patients often need to be kept in hospital for management of fluids and stoma bags, in specialist units, and at substantial cost. Fistula patients are also typically at risk of malnutrition due to the lost capacity to absorb food. Fistula patients may also suffer skin damage around the stoma site because small intestine contents are damaging to skin, and they may suffer more frequent bag leaks due to the high outputs putting pressure on the bag seal. Furthermore, the fluid loss and stoma management may be exacerbated by eating, meaning fistula patients may need to be placed nil-by-mouth. Due to the inadequate nutrition, they often need to be given replacement nutrition through a vein—called 'parenteral nutrition', which is expensive and is deemed a risk to the patient due to the possibility of line infections and severe sepsis (can cause death), and some patients experience liver damage. Typically, fistula patients are left in this predicament for many months before it is safe to operate to close their fistulas, sometimes being required to stay in hospital for the duration of this whole period.

In some patients with a fistula, it is possible to access the distal gut through a tube or catheter. It may be desirable to improve nutrition of patients with fistulas by recycling the content from a fistula into the downstream gut.

A recycling device is anticipated to make these problems easier to manage in the certain fistula patients—particularly dehydration, nutrition and stoma care—and therefore reducing costs.

It is also anticipated that the nutrient recycling device 1 may be used to bypass a segment in the patient's body, by recycling the contents from a first opening 3 and returning the contents to a second opening 4. For example, the device 1 may be useful in other organ systems to control outputs and/or input such as content in the urinary tract.

Stoma Bag and Patient

Figure 1:
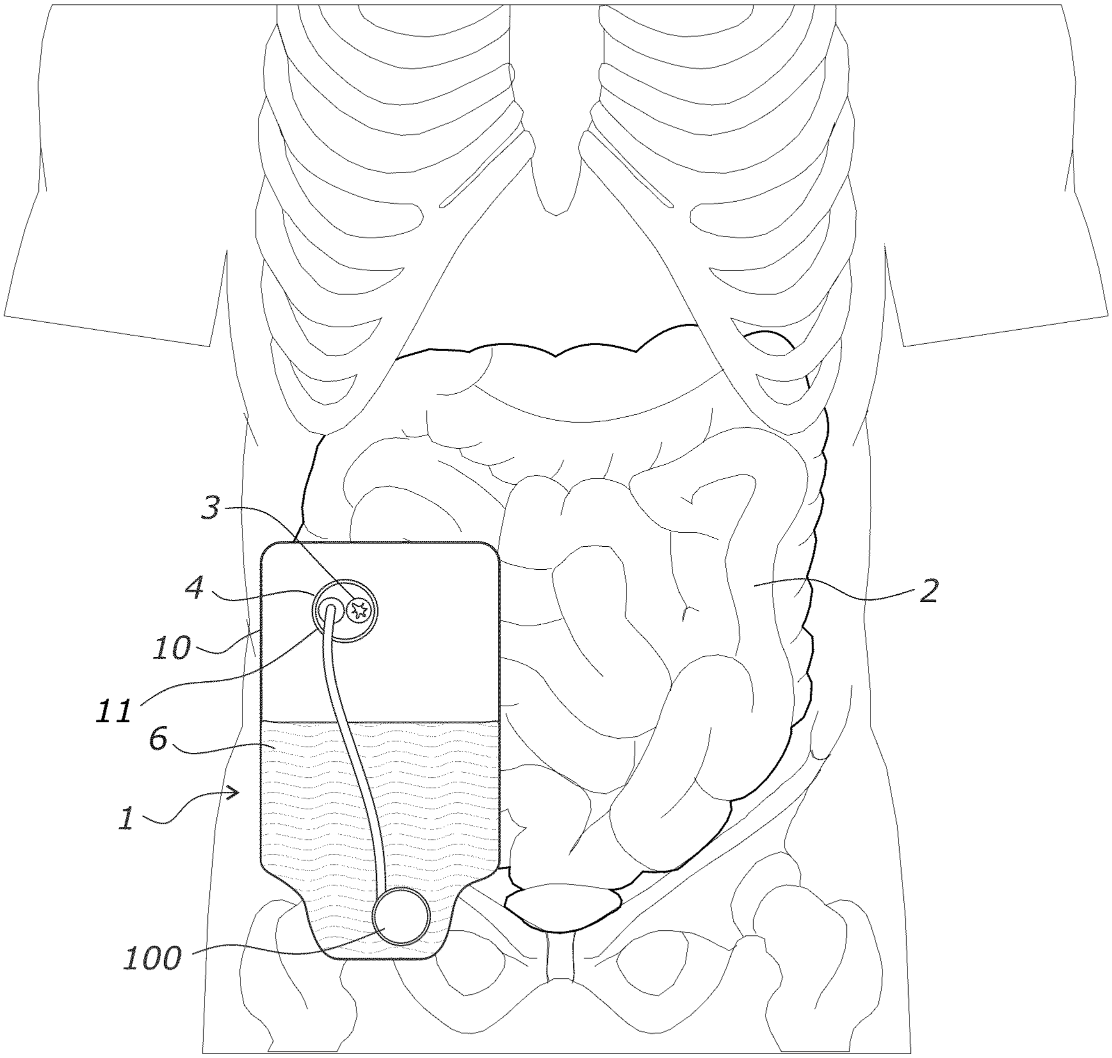
FIG. 1 shows a schematic of a patient and the nutrient recycling device.

With reference to FIG. 1, in at least some configurations, the nutrient recycling device 1 comprises a pump 100 incorporated with a bag 10, adapted to recycle fluid and nutrients from digestive contents 6 from a first opening 3 of a gastrointestinal tract to a second opening 4 of the gastrointestinal tract. In at least some embodiments the bag 10 is a stoma bag. The nutrient recycling device 1 is adapted to be worn externally by a patient.

In at least some embodiments, the stoma bag 10 comprises a bag opening 11. In one configuration, the bag opening 11 is In at least some embodiments positioned over a first opening of the gastrointestinal tract 3. In at least some embodiments, the bag opening 11 is positioned over a stoma 5 of a patient. The stoma 5 is an opening on the surface of a patient's abdomen configured to allow access to the first and second opening of the gastrointestinal tract.

In at least some embodiments, the area of the bag opening 11 is larger than the corresponding stoma 5 which it fits over. In at least some embodiments, the bag opening 11 is located towards an upper end of the stoma bag 10.

The stoma 5 is an opening on the surface of the abdomen, and may provides access to the proximal opening 3 and distal opening 4 of the ileum. In at least some embodiments, the flow pathway of the digestive contents 6 is shown by arrows in FIG. 2A. In at least some embodiments, the proximal opening 3 of the ileum 2 is an inlet and is configured to evacuate the patient's digestive contents 6 into the stoma bag 10. The distal opening 4 of the ileum 2 is in at least some embodiments an outlet and is configured to receive digestive contents 6 from the stoma bag 10.

In at least some embodiments, the stoma bag 10 comprises an attachment portion. In at least some embodiments the attachment portion is located at an exterior sidewall of the stoma bag 10.

Optionally, the attachment portion comprises an adhesive backing to adhere the stoma bag 10 to the skin of a patient. In at least some embodiments, the adhesive is located around the perimeter of the bag opening 11.

In one configuration, the attachment portion is integrated with the side wall of the stoma bag 10.

In another configuration, the attachment portion is separable from the stoma bag 10.

In one configuration, the attachment portion remains adhered to the patient, while the stoma bag 10 can be detached and reattached as desired. A separable stoma bag 10 may be implemented if it is desirable to allow the stoma bag 10 to be removed for replacement, or to attend to the internal components of the stoma bag 10. For example, the stoma bag 10 may be replaced every few days, or as required.

Optionally, the stoma bag 10 comprises a rubber ring on a sidewall, and the attachment portion comprises a complimentary rubber ring adapted to connect and disconnect the stoma bag 10 from the attachment portion. It is anticipated that other connection mechanisms known in the art may be implemented to connect and disconnect the stoma bag 10 from the attachment portion.

Optionally, the nutrient recycling device 1 can be further supported and/or secured to a patient by attaching the stoma bag 10 to a belt or similar article worn by the patient, such as clips, buckles, or straps for example.

In at least some embodiments, the stoma bag 10 comprises a generally rectangular shape. Optionally, the stoma bag 10 comprises an oval-like shape.

In at least some embodiments, the stoma bag 10 has a capacity of 500 mL to 2000 mL. In at least some embodiments, the stoma bag 10 has a capacity of 800 mL to 1200 mL.

In at least some embodiments, the stoma bag 10 length is 10 cm to 30 cm long. In at least some embodiments, the stoma bag 10 length is 12 cm to 20 cm long.

In at least some embodiments, the stoma bag 10 width is 10 cm to 25 cm wide. In at least some embodiments, the stoma bag 10 width is 12 cm to 16 cm wide.

It is anticipated the size of the stoma bag 10 may need to be shaped to different custom sizes depending on the configuration of the stomas or fistula opening(s) and the patient's body habitus. For example, larger stoma bags 10 may be necessary for patients with fistulas due to the generally higher output of digestive contents 6.

In at least some embodiments, the stoma bag 10 comprises an impermeable plastic, for example polyethylene.

In at least some embodiments, the stoma bag 10 comprise a material impermeable to the digestive contents 6. In at least some embodiments, the stoma bag 10 also comprises a material impermeable to the odours and other gases from the digestive contents 6.

In at least some embodiments, the stoma bag 10 comprises a flexible material. In at least some embodiments, the stoma bag 10 can flatten when the bag is not full with digestive contents 6, and swell when digestive contents 6 enter the bag 10. An feature of a flexible stoma bag 10 is to help the nutrient recycling device 1 be compact. Stoma bags are generally inexpensive and can therefore be disposed or replaced after a single or use (or a few uses). A disposable or replaceable stoma bag 10 may mean that a patient or a caregiver does not need to clean the bag 10 between separate uses.

In one configuration, the stoma bag 10 is transparent to reveal the internal contents of the bag 10. In another configuration, the stoma bag 10 is opaque and may be a similar color to the patient's skin. This may assist in concealing the contents of the bag 10, and make the nutrient recycling device 1 more discrete for the patient to wear.

Optionally, the nutrient recycling device 1 comprises an external cover adapted to be removable or partially removable from the stoma bag 10. In one configuration, the stoma bag 10 is transparent, and the external cover is opaque. For example, the external cover optionally comprises a flap configured to be lifted to reveal the internal contents of the bag 10 such as the digestive contents 6, or the position of the pump 100. Alternatively, the position of the pump 100 may simply be felt by the patient or medical caregiver. Optionally, the external cover is a similar color to the patient's skin.

Stoma Bag and Pump Connection

The nutrient recycling device 1 in at least some embodiments comprises a pump 100. The pump 100 is In at least some embodiments incorporated with the stoma bag 10. In some configurations, the pump 100 is incorporated inside the stoma bag 10. In other configurations, the pump 100 is incorporated external to the stoma bag 10. In yet another configuration, the pump 100 is incorporated with the bag 10 by forming at least part of the wall of the bag. Optionally, the pump 100 is incorporated with the bag 10 by an attachment means.

In some configurations, the nutrient recycling device 1 is configured to pump liquid and partially liquid digestive content 6.

The digestive content 6 may enter the stoma bag 10 through the first opening 3 of the gastrointestinal tract and is configured to allow inflow of digestive contents 6 into the bag 10. In at least some embodiments, the digestive content 6 is collected towards the bottom of the stoma bag 10 due to gravity, and the pump 100 is immersed in the digestive contents 6. In at least some embodiments, the digestive content 6 enters the bag 10 through natural propulsion of the gastrointestinal tract such as due to smooth muscle contractions.

Optionally, an inlet conduit (not shown) can be configured to guide the digestive content 6 from the proximal opening 3 of the ileum 2 to or towards the pump body 101.

Optionally, medicament can be added into the stoma bag 10 or conduit 20, 30 to be pumped into the distal segment of the gastrointestinal tract. For example, antibiotics such as metronidazole or vancomycin may be used to treat infections such as *Clostridium difficile* infections. Alternatively, probiotics such as beneficial bacterial populations may be introduced to re-establish or alter a patient's colonic microbiome.

In at least some embodiments, the pump 100 comprises a pump inlet 102 which communicates with the interior of the stoma bag 10. In at least some embodiments the pump inlet 102 is in fluid communication with or immersed in) the digestive content 6 in the stoma bag 10.

In at least some embodiments, the digestive content 6 is pumped from the pump 100 to the second opening 4 of the gastrointestinal tract. In at least some embodiments, the digestive content 6 exits the pump 100 from a pump outlet 103. In at least some embodiments, the pump 100 is able to drive the digestive contents 6 against gravity.

The connection of the nutrient recycling device 1 to the proximal opening 3 and the distal opening 4 can be established during an ileostomy or other medical procedure.

In some configurations, connecting the nutrient recycling device 1 during the procedure means that the digestive content 6 can be recycled into the distal gastrointestinal tract without further invasive procedures for surgery.

Recycling digestive content 6 to the second opening 4 which is downstream from the first opening 3 soon after the gastrointestinal tract distal to the ileum has healed may reduce patient and economic burden of stoma-related dehydration.

Early stimulation of the distal gastrointestinal tract may also reduce the likelihood of renal failure, electrolyte and/or acid—base imbalance which may cause severe illness and slow recovery times.

Furthermore, the nutrient recycling device 1 may reduce the loss of colonic microbiome and decrease the inoperative colon period. The device 1 may decrease the short-term and/or long-term negative effects on bowel function due to ileostomy diversion.

Conduit/Tubing

In at least some embodiments, the nutrient recycling device 1 comprises a conduit 20, 30. In at least some embodiments, the conduit 20, 30 provides a flow pathway for the digestive content 6 to flow from the pump 100 through to the upstream location 4' in the patient's gastrointestinal tract.

As illustrated in FIGS. 10A and 10B, in some configurations, the nutrient recycling device 1 comprises a delivery catheter 45 which extends to the upstream location 4'. The nutrient recycling device 1 as shown in FIGS. 10A and 10B is shown to be off on a side of the patient for illustrative purposes only so that the internal organs are not covered. When the nutrient recycling device 1 is in use, the bag 10 can be positioned as required for functioning and/or for comfort.

In some configurations, the conduit 30 acts as the delivery catheter 45 and extends from the stoma bag 10 and directly enters the upstream location 4'. In other configurations, the delivery catheter 45 provides an extension from the conduit 30 to extend into the upstream location 4' at the desired location. The desired location in at least some embodiments is in the small intestine where nutrient absorption in the gastrointestinal system occurs.

In some configurations, the delivery catheter 45 which extends into the upstream location 4' is an enteral feeding tube such as a gastro jejunal tube. In at least some embodiments, the delivery catheter 45 is flexible or semi-flexible so it can be directed into the patient and situated in the desired location.

In some configurations, the second opening 4 is located downstream from the first opening 3 in the gastrointestinal tract in a direction towards the anus. In one configuration, the first opening 3 is a proximal stoma, and the second opening 4 is a distal stoma. In at least some embodiments, the delivery catheter 45 includes an output end of the delivery catheter 45 which is positioned downstream in the gastrointestinal tract from the first opening 3 configured to reintroduce the digestive contents back into a patient.

In other configurations, the upstream location 4' is located upstream in the gastrointestinal tract from the first opening 3 towards the stomach. The digestive contents 6 contained within the bag 10 of the nutrient recycling device 1 is driven to the upstream location 4' within the gastrointestinal system. As illustrated in FIGS. 10A and 10B, it is anticipated that the delivery catheter 45 can be inserted and navigated to different locations in a patient, so that an output end of the delivery catheter 45 is located in the desired location to reintroduce the digestive contents back into a patient. FIG. 10A shows that the delivery catheter 45', 45" can be provided through the nasal cavity or through the abdomen.

FIG. 10B shows the delivery catheter 45' can be inserted back through the first opening 3. In at least some embodiments, the output end 47 of the delivery catheter 45 is positioned upstream from the first opening 3.

As shown in FIG. 10A, in some configurations, the delivery catheter 45' is inserted through a nasal cavity of the patient. In at least some embodiments, the delivery catheter 45' is directed from the nose to the upstream location 4' (upstream from the first opening 3).

In other configurations, the delivery catheter 45" is connected through a patient's skin and into a sidewall of the gastrointestinal tract so that digestive contents 6 can be delivered from the bag 10 back into the gastrointestinal system to the upstream location 4' upstream the first opening 3.

This may typically be performed by connection of the catheter 20 arising from the pump 100 to a delivery catheter 45" which is a percutaneous gastrojejunal feeding tube. Percutaneous gastrojejunal feeding tubes may be placed through the abdominal wall, before passing through the pylorus of the stomach and into the jejunum, providing intermittent or continuous access to the small bowel. The catheter 20 leading from the pump is In at least some embodiments connected directly to the inlet of a gastrojejunal tube. In some configurations, the gastrojejunostomy tube may be anchored in the stomach across the abdominal wall by the use of a balloon.

In other configurations, the upstream location 4' can be accessed by a percutaneous enterostomy procedure, where a needle is instrumented into the gut through the abdominal wall to provide an access port, such as under imaging or endoscopic guidance.

In yet another configuration as shown in FIG. 10B, the deliver catheter 45' is inserted back upstream through the first opening 3 of the gastrointestinal tract to the upstream location 4'. In this configuration, the digestive contents 6 first enters the stoma bag 10 through the first opening 3 after passing through a functioning segment of the small intestine. The collected digestive contents 6 are then pumped back upstream through the first opening 3, where the delivery catheter 45''' provides a pathway to the upstream location 4' at the desired upstream location in the gastrointestinal tract.

There may be one or multiple upstream openings to release the digestive contents 6 back into the gastrointestinal tract. The digestive content 6 re-passes through the functioning segment of the small intestine. Re-passing may be undertaken multiple times to increase the time that gut contents are in contact with the lumen to increase overall absorption.

As shown in the schematic at FIG. 10B, in some configurations the delivery catheter 45 includes an anchor 46 configured to keep the delivery catheter 45 in a desired region of the small intestines. In at least some embodiments, the anchor 46 is able to resist movement against the natural propulsion of the gastrointestinal tract. In at least some embodiments, the digestive contents 6 can flow past the anchor. This may be particularly useful where the delivery catheter 45' is inserted back upstream into the gastrointestinal tract.

In some configurations, the anchor 46 is inserted into the stomach (not shown), and the delivery catheter 45 is supported from the stomach. In at least some embodiments, the anchor includes arms which engage against the stomach wall to hold the delivery tube in place. In some configurations, the anchor comprises a T-shape.

In other configurations, the anchor is a stent or vacuum collar (as shown in FIG. 10) to engage with the inner walls of the gastrointestinal tract to keep the catheter in place. In at least some embodiments, the delivery catheter 45 includes perforations or apertures towards the output end of the tube to provide exit paths for the digestive contents 6.

In yet another configuration, the anchor 46 is located at or towards the first opening 3 of the gastrointestinal tract (not shown). Optionally, the anchor is a base plate which engages against the outer surface at the first opening 3 to hold the delivery catheter 45 in place. In another optional configuration, the anchor is a pouch contained inside a stoma bag 10 near to the first opening 3. The delivery tube 45''' extends upwards from the anchor 46 at the first opening 3. It is anticipated that the delivery tube 45 may be introduced into the patient through other pathways to get to the desired location as known by a skilled person in the art.

In some configurations, a first portion of the conduit 20 is located within the stoma bag 10. In at least some embodiments, a second portion of the conduit 30 is adapted to be inserted into the distal opening 4 of the ileum 2.

In at least some embodiments, the conduit 20, 30 is separable from the stoma bag 10. A separate conduit 20, 30 may be utilized when a patient changes their stoma bag 10. For example, a portion of the conduit 30 can remain in the distal opening 4 of the ileum 2, while the stoma bag 10 is removed.

In at least some embodiments, the diameter of the second portion of the conduit 30 is smaller than the diameter of the second opening 4 in a stretched state. In at least some embodiments, the diameter of the conduit 20, 30 is large enough to reduce resistance of flow and/or to reduce the chance of blockages.

In at least some embodiments, the conduit 20, 30 is a continuous conduit comprising a first portion of the conduit 20 and a second portion of the conduit 30.

Optionally, the pump 100 comprises ridges 114, as shown in FIG. 3C to engage with a first end 21 of the first portion of the conduit 20.

In at least some embodiments, the conduit 20, 30 is hollow. In at least some embodiments, the first portion of the conduit 20 conveys the digestive contents 6 from the first end 21 to the second end 22 of the first portion of the conduit 20.

Optionally, the first portion of the conduit 20 comprises a one way valve (not shown) to preclude backflow of digestive content 6 in the first conduit 20.

Optionally, a flange 12 is connected to the conduit 20, 30. Optionally, the flange 12 comprises a rigid material. In at least some embodiments, the flange 12 stabilizes the conduit 20, 30.

The flange 12 illustrated extends radially from the outer sidewall of the conduit 30. In at least some embodiments, the flange body 12 is located inside the stoma bag 10. In at least some embodiments, the flange 12 is located external to cavity the second portion of the conduit 30 is inserted into. In at least some embodiments, the flange prevents the first portion of the conduit 20 from migrating further into the gastrointestinal tract.

Optionally, the flange 12 comprises apertures 17 for suturing the flange to the patient or attaching to a bag.

In one configuration, the flange 12 comprises a circular cross-section.

Figure 2A:
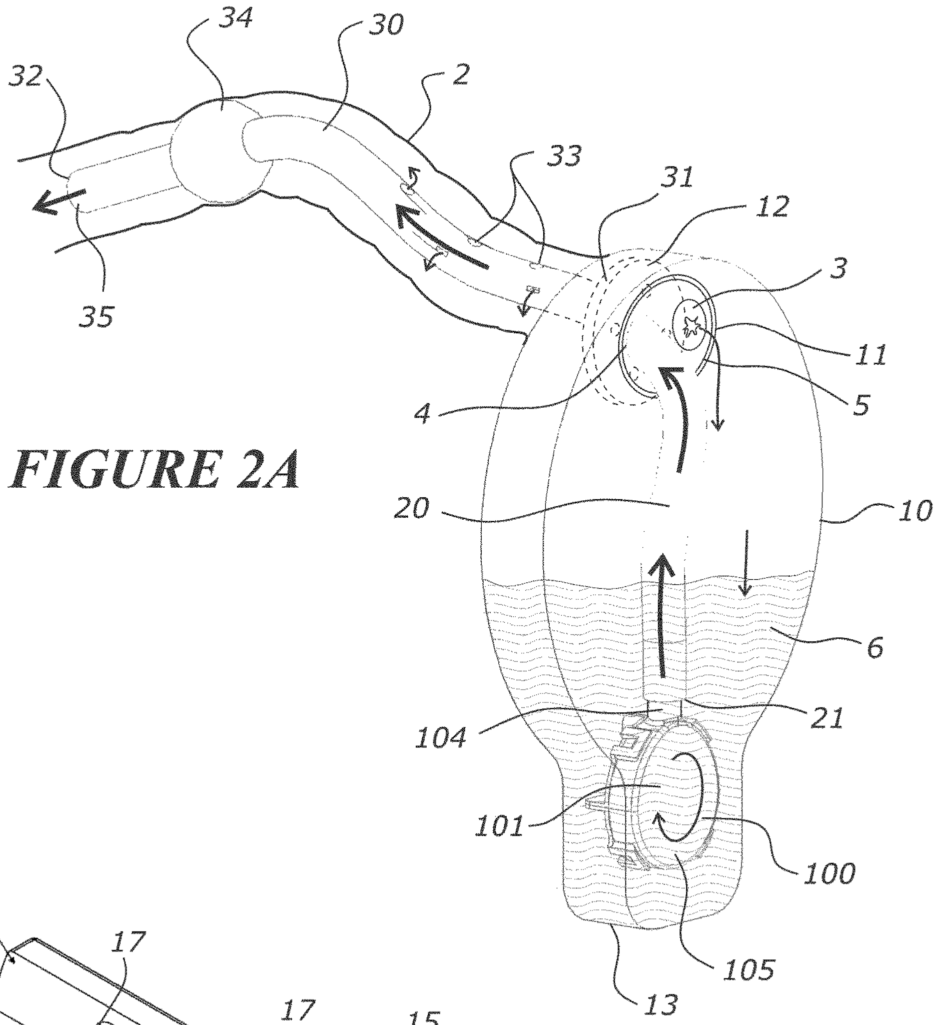
Figure 2B:
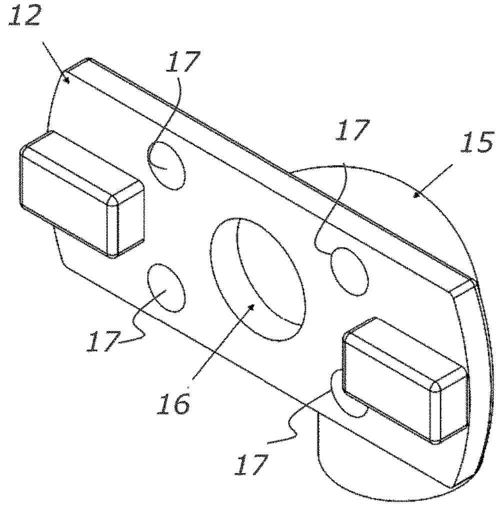

In another configuration, the flange 12 comprises a rectangular cross-section as shown in FIG. 2B.

In at least some embodiments, the flange 12 comprises an opening 16 configured to receive the conduit 20, 30.

Optionally, the flange 12 comprises an elbow 15 configured to extend into the stoma bag 10. In at least some embodiments, the flange elbow 15 bends towards the bottom of the stoma bag 10. The conduit 20, 30 is configured to be guided by the elbow 15 towards the bottom of the stoma bag 10. The elbow 15 is in at least some embodiments rigid. The elbow 15 may be low profile.

In at least some embodiments, the length of the first portion of the conduit 20 is adapted to allow the pump 100 to be located towards the bottom of the stoma bag 10 as best shown in FIGS. 2A and 4A. Optionally, the first portion of the conduit 20 is rigid or semi-rigid to locate the pump 100 in the desired position, such as the bottom of the stoma bag 10.

Optionally, the pump 100 comprises a pump connection piece 104. The pump connection piece 104 in at least some embodiments connects the pump body 101 to a first end 21 of conduit 20.

Optionally the nutrient recycling device 1 comprises a first conduit 20 separate from a second conduit 30. In at least some embodiments, the first conduit 20 connects the pump 100 to the distal opening 4. In at least some embodiments, a first end 21 is connected to the pump 100 and a second end 22 is located at the second opening 4. In at least some embodiments, the first conduit 20 is located within the stoma bag 10.

Optionally, the nutrient recycling device 1 comprises a second conduit 30 separate to the first conduit 20. In at least some embodiments, the second conduit 30 connects the bag opening 11 to a distal portion of the ileum 2.

In at least some embodiments, the second conduit 30 is located external to the stoma bag 10.

The flow pathway of the digestive contents 6 from a first end 31 to a second end 32 of the second conduit 30 is shown by arrows in FIG. 2A.

In at least some embodiments, the first portion of the conduit 20 and the second portion of the conduit 30 comprises the same material. For example, the conduit 20, 30 comprises a medical-grade silicone, however other catheter materials such as polyurethane, PVC or latex rubber are also options.

In other configurations, the first conduit 20 and the second conduit 30 comprises different materials. For example, the first conduit 20 comprises a semi-rigid material to help stabilize the interior components in the stoma bag 10. The second conduit 30 may comprise a more flexible material to help deform to the contour of the ileum 2.

Second Conduit Apertures

In at least some embodiments, the second portion of the conduit 30 comprises one or more apertures 33 on the sidewall of the conduit 30. In at least some embodiments, the apertures 33 allow fluid communication of the digestive contents 6 from the second portion of the conduit 30 to the ileum 2.

In at least some embodiments, only a small portion of the flowing digestive content 6 exits through the apertures 33. In at least some embodiments, the digestive content 6 deposited in this area can be absorbed by the ileum 2.

In at least some embodiments, the main flow of the digestive contents 6 exists through an outlet 35 at the second end 32 of the second conduit 30. In some configurations all of the flowing digestive content 6 exits through the outlet 35.

The nutrient recycling device 1 in at least some embodiments limits fluid and nutrient loss from a stoma 5, as digestive contents 6 is recycled back into the gastrointestinal tract.

The nutrient recycling device 1 may reduce some of the common complications of ileostomies. Use of the nutrient recycling device 1 may decrease costs of stoma patients to hospitals due to reduced need for rehydration and other medications and/or readmission to the hospital associated with stomas.

Inflatable Cuff

In at least some embodiments, the second portion of the conduit 30 of the nutrient recycling device 1 comprises an inflatable cuff 34. In at least some embodiments, the inflatable cuff 34 comprises a circular cross-section.

The inflatable cuff 34 in at least some embodiments operates between a deflated condition and an inflated condition.

In the deflated condition, the inflatable cuff 34 is in at least some embodiments the same or similar diameter as the second portion of the conduit 30.

In the inflated condition as shown in FIG. 2A, the inflatable cuff 34 comprises a diameter similar to or greater than the diameter of the second portion of the conduit 30. In at least some embodiments, in the inflated condition, the inflatable cuff presses against the inner wall of the ileum 2 to stabilize the second conduit 30. The inflatable cuff 34 may help the nutrient recycling device 1 stay the desired position. This may help permit the patient move around in their everyday life without having to worry about the position of the nutrient recycling device 1.

In at least some embodiments, the inflatable cuff 34 is located external to the second portion of the conduit 30. In at least some embodiments, the inflatable cuff 34 in the inflated condition does not decrease to diameter of the conduit 30.

In some configurations, the inflatable cuff 34 can be inflated with saline. In at least some embodiments, the saline is delivered by a separate inflating conduit (not shown). Optionally, the inflating conduit can be removed once the second portion of the conduit 30 is secured in the desired location.

Alternatively, the cuff 34 is a vacuum or negative pressure cuff.

In some configurations, an inflating mechanism is integrated with the conduit 30 of the nutrient recycling device 1.

Drainage

In some configurations, the stoma bag 10 comprises a drainage bag opening 13. The drainage bag opening 13 is configured to provide an outlet to empty digestive contents 6 from the stoma bag 10.

Draining the stoma bag 10 may be necessary in the early stages of recovery from colorectal surgery, where the distal gastrointestinal tract is not ready to receive digestive contents 6 yet. The recycling function of the nutrient recycling device 1 may only commence once the patient is recovered sufficiently from the colorectal surgery (usually 1-2 weeks), which is typically confirmed by a radiological leak test of the colorectal join. Optionally, the recycling function of the nutrient recycling device 1 can commence sooner after surgery, for example if stoma output is very high, slightly before the patient is recovered from the colorectal surgery.

Draining the stoma bag 10 may be desired in the later stages of recovery if the medical practitioner wants to recycle some of the digestive contents 6 to the distal gastrointestinal tract, but not all the flow.

In at least some embodiments, the drainage bag opening 13 is located at or towards the lower end of the stoma bag 10. In one configuration, the drainage bag opening 13 is a defined outlet at the lower end of the stoma bag 10, for example with a circular cross-section. In other configurations, the drainage bag opening is an opening along the lower end of the stoma bag 10.

In some configurations, the drainage bag opening 13 is adapted to receive the pump 100. For example, the pump 100 may be reinserted through the drainage opening 13 after the patient changes their stoma bag 10.

In at least some embodiments, the drainage bag opening 13 is re-sealable. For example, a clip, Velcro, reversible adhesive, or other releasable sealing mechanisms known to the art may be used. Optionally, the lower end of the stoma bag 10 can be rolled over itself one or more times to close the drainage bag opening, in at least some embodiments, prior to applying this mechanism of clipping or Velcro for example.

Pump Mechanism

In at least some embodiments, the pump 100 of the nutrient recycling device 1 as shown in FIGS. 2A and 3A-C comprises a pump body 101.

The pump 100 in at least some embodiments blocks or tolerates partially digested particulate matter and avoids clogging of internal parts. Optionally, the pump 100 actively makes the partially digested particulate matter smaller or the digestive contents 6 more fluid. In one configuration, the pump 100 comprises a grinder to make the partially digested particulate matter smaller. In another configuration, the pump 100 comprises one or more blades to cut the partially digested particulate matter into smaller particles.

The pump 100 in at least some embodiments comprises a housing. In at least some embodiments, the housing comprises a substantially circular cross-section.

In one configuration, the pump 100 comprises a top housing 105. In at least some embodiments, the pump 100 also comprises a bottom housing 106. The top 105 and bottom housing 106 may limit larger partially digested particulate matter from entering the interior portion of the pump.

Alternatively, a filter, such as a grate or sieve, incorporated with the housing can limit larger partially digested particulate matter from entering the interior portion of the pump.

Limiting larger partially digested matter can help prevent the pump 100 and/or the conduit 20, 30 from clogging. It may reduce the likelihood of blockages as a blocked conduit 20, 30 may increase resistance or drag in the flow pathway.

In at least some embodiments, the top housing 105 is connected to the bottom housing 106. Optionally, the top housing 105 is separable from the bottom housing 106.

Optionally, the top housing 105 is connected to the bottom housing 106 by fastening members 107 as best shown in FIG. 3A. The fastening members 107 can be a clasp, snap fit mechanism, friction grip mechanism, complementary threaded members or adhesive. It is anticipated that other fastening members known to the art may be used to connect the top housing 105 and the bottom housing 106.

In at least some embodiments, the pump 100 of the nutrient recycling device 1 comprises a movable component 108. In at least some embodiments, the movable component 108 is circular.

In at least some embodiments, the movable component 108 is an impeller. In at least some embodiments, digestive contents 6 enter the body 101 of the pump 100 through the pump inlet 102. In at least some embodiments, the impeller 108 is adapted to be fully or partially immersed in the digestive contents 6 when in use. In at least some embodiments, the nutrient recycling device 1 comprises an inlet 102 located at the base of the bottom casing 106.

The impeller 108 is a rotating component in the pump 100 configured to displace the fluid or partially fluid digestive contents 6. In at least some embodiments, the inlet 102 is located at or towards the axis of rotation of the pump 100.

In at least some embodiments, the impeller 108 comprises fins 109 as shown in FIGS. 3A and 3B to displace the digestive contents 6. In at least some embodiments, the impeller 108 imparts centrifugal force to the digestive content 6 particles, and drives the digestive content 6 radially outwards towards the inner sidewall of the top housing 105 of the pump. Optionally, the impeller 108 in parts share forces that may shred the digestive contents 6 into smaller particles.

In at least some embodiments, the fins 109 extend from the underside of the movable component 108. In at least some embodiments, the fins 109 extend on a plane orthogonal to the plane of the body of the movable component 108.

As the impeller 108 displaces the digestive content 6 in the pump 100, the digestive content 6 is in at least some embodiments driven from the center of rotation of the impeller radially outwards.

In at least some embodiments, the impeller 108 drives the digestive contents 6 through a flow channel 113 as shown in FIG. 3C. The flow channel 113 in at least some embodiments leads to the pump outlet 103.

Optionally, the pump 100 comprises a flow channel 113 with increasing area along the flow direction. In at least some embodiments, the increased area along the flow channel 113 reduces flow velocity of the digestive content 6 which increases static pressure to help overcome resistance of the pump 100.

In one configuration, the movable member 108 at least partially comprises a magnetic or ferromagnetic element 110 as shown in FIGS. 3B, 3C, and 5B. In one configuration, the moveable member 108 is at least partially magnetic or ferromagnetic.

Alternatively, the moveable member 108 comprises a separable magnetic or ferromagnetic element 110. The magnetic or ferromagnetic element 110 is configured to be coupled with a complimentary magnetic or ferromagnetic piece 152. The magnetic or ferromagnetic element 110 in at least some embodiments moves as the complimentary magnetic or ferromagnetic piece 152 moves. In one configuration, the complimentary magnetic or ferromagnetic piece 152 rotates. In at least some embodiments, the magnetic or ferromagnetic element 110 of the pump also rotates as the complimentary magnetic piece 152 rotates.

In at least some embodiments, the pump 100 is adapted to be driven by an external pump actuator 150. A pump actuator 150 external to the sealed bag 10 (described in more detail later), reduces the likelihood of the leakages.

In at least some embodiments, the magnetic element 110 comprises a cylindrical shape as best shown in FIG. 3B. It is anticipated, the magnetic or ferromagnetic element 110 may comprise other shapes such as a spherical or rectangular shape.

In at least some embodiments, the pump 100 comprises a durable biocompatible medical grade plastic. In at least some embodiments, the pump 100 is tolerant to a fluid environment, digestive enzymes and pH between 5.5-8.

Optionally, the pump 100 comprises a biofilm-resistant covering, or an antibacterial surface, e.g., when the pump 100 is submerged in digestive content 6.

In at least some embodiments, the pump 100 comprises material configured to be easily sterilized e.g. by gamma sterilisation.

In at least some embodiments, the pump 100 comprises a support 111 along the axis of rotation. In at least some embodiments, the support 111 extends from the underside of the movable component 108.

As shown in FIG. 3C the bottom housing 106 optionally comprises a complimentary orifice 112 adapted to receive the support 111. In at least some embodiments, the support 111 and complimentary orifice 112 stabilises the movable component 108 as it moves.

Pump Locations

In one configuration, as shown in FIG. 4A, the pump 100 is located towards a lower end of the stoma bag 10.

In another configuration, as shown in FIG. 4B, the pump 100 is located between the top and bottom ends of the stoma bag 10.

In one configuration, the pump 100 is incorporated with the stoma bag 10 as it is located within the bag. An internal pump 100 is in fluid communication with the digestive contents 6. The material properties of the first conduit 20 and/or the pump 100 can bias the pump 100 towards the bottom of the stoma bag 10 (FIG. 4A). Material properties may include the flexibility of the first conduit 20, or the weight of the internal components.

Alternatively, the material properties of the first conduit 20 and/or the pump 100 can allow the pump 100 to float or partially float in the digestive contents 6 in the stoma bag 10 (FIG. 4B). For the avoidance of doubt, the use of the word float means not attached to the bag in this context. It is intended that the pump 100 be fully or partially immersed in the digestive contents 6, as the bag 10 fills.

In another configuration, the pump 100 is located external to the stoma bag 10 as shown in FIG. 4C.

In at least some embodiments, the external pump 100 comprises a pump inlet 102 which receives the digestive contents 6 from the stoma bag 10.

Optionally, a first external conduit 40 connects the stoma bag 10 to the external pump 100. In at least some embodiments, the first external conduit 40 is connected at or towards the bottom of the stoma bag 10. Optionally, gravity helps deliver the digestive contents 6 from the stoma bag 10 to the external pump 100 if the first external conduit 40 is connected at or towards the bottom of the stoma bag 10.

In at least some embodiments, the stoma bag 10 comprises a first conduit opening adapted to allow the first external conduit 40 to communicate with the inside and the outside of the bag 10. In at least some embodiments, the first conduit opening is sealed against the first external conduit 40 to prevent leakage from within the bag 10.

In at least some embodiments, the external pump 100 comprises a pump outlet 103 adapted to release the digestive contents 6 from the stoma bag 10. Optionally, a second external conduit 50 connects the pump outlet 103 to the stoma bag 10. In at least some embodiments, the stoma bag 10 comprises a second conduit opening adapted to allow the second external conduit to communicate with the inside and the outside of the bag 10. In at least some embodiments, the second conduit opening is sealed against the second external conduit to prevent leakage from within the bag 10.

Optionally, the external pump 100 is separable from the stoma bag 10. In at least some embodiments, inlet and/or outlets of the stoma bag 10 configured to lead to and from the external pump 100 comprises a one way valve or closing mechanism to prevent communication of digestive contents 6 when the external pump 100 is not connected.

In at least some embodiments, the stoma bag 10 comprises a second bag opening configured to allow communication of digestive contents to an external pump 100.

Optionally, the stoma bag 10 comprises a sealing plate. The sealing plate in at least some embodiments comprises an aperture configured to be located at the second bag opening. The sealing plate is configured to allow passage of wires or other internal bag components to an external pump 100. The sealing plate in at least some embodiments allows passage of these components while precluding leakage of the digestive contents 6 from within the stoma bag 10.

Incorporated Pump

The pump 100 can be incorporated into the stoma bag 10 by being attached to a side wall of the bag 10. In one configuration, the pump 100 is attached to the inner side wall of the bag 10. In another configuration, the pump 100 is attached to the outer side wall of the bag 10.

In another configuration, the pump housing forms at least part of the bag wall.

In one configuration, the pump 100 can be adhered to the side wall of the stoma bag 10 by plastic welding, chemical adhesion or other similar adhesion methods known in the art.

In another configuration, the pump 100 is incorporated into the stoma bag 10 by fastening means such as clips, clasps, buckles, Velcro, zip, slide fastener, snap fasteners, magnets or other fasteners known in the art.

Optionally, the pump 100 comprises a slit in its housing which engages with a complementary flange on the stoma bag 10 to secure the pump 100 to the bag 10.

In yet another configuration, the stoma bag 10 comprises a pouch (not shown) adapted to locate the pump 100 at the desired position relative to the stoma bag 10. In at least some embodiments, the pouch is incorporated into a side wall of the stoma bag 10. In at least some embodiments, the pouch comprises a pouch opening to allow fluid communication between the digestive contents 6 and the pump 100. In another configuration, the inner side wall of the stoma bag 10 comprises a collar or clasp configured to clasp around the conduit 20. It is anticipated that other clasp, wrapping or fastening mechanism from within the stoma bag 10 can be used to position the pump 100 within the stoma bag 10.

In at least some embodiments, the side compartment adapted to store the pump 100 is located at or towards the pump 100, so the pump actuator 150 and the pump 100 can be in close contact.

In another configuration, the stoma bag 10 comprises magnets adapted to attract the pump 100 in the desired location.

Pump Actuators

In at least some embodiments, the nutrient recycling device 1 comprises a pump actuator 150 as shown FIG. 4C and FIGS. 5A-5C to drive the pump 100. In at least some embodiments, a coupling mechanism couples the pump actuator 150 to the pump 100.

In at least some embodiments, a magnetic coupling couples the pump actuator 150 to the pump 100. Alternatively, a mechanical coupling couples the pump actuator 150 to the pump 100.

In at least some embodiments, as represented in FIGS. 5A-5B, the pump actuator 150 is separable from the pump 100. A separable pump actuator 150 may keep the nutrient recycling device 1 compact, and lightweight which may be important to a patient as they may need to wear the nutrient recycling device 1 for extended periods of time.

In at least some embodiments, when in use, the pump actuator 150 engages with the pump 100 or is placed in close proximity to the pump by the patient. In one configuration, the patient connects the pump actuator 150 to the pump. In another configuration, the patient places the pump actuator 150 in close proximity to the pump in order for coupling between the pump actuator 150 and pump to drive the pump.

Alternatively, as represented in FIG. 4C, the pump actuator 150 can be integrated with the pump 100. The nutrient recycling device 1 being a one unit device may limit the management required by the patient or medical caretakers.

Optionally, the component comprising the pump actuator 150 comprises an integrated battery. The patient can replace the batteries when they run flat, or optionally they can charge the pump actuator unit separately.

Optionally, as shown in FIG. 5A, the pump actuator 150 comprises a power cord 151. In at least some embodiments, the power cord 151 temporarily connects the nutrient recycling device 1 to an electricity supply. Optionally, the power cord 151 is a mains cable, adapted to be connected to a wall socket. Alternatively, the power cord 151 can be adapted to be connected to a USB or similar port, and may be powered by a portable power bank or other battery-like supply. Optionally, the power cord 151 is connected to a portable power supply such as a battery pack. The portable power supply can optionally be carried by the patient close to the stoma bag on their belt for example. The power supply can be worn on their belt by a clip or other fastening means, or in a separate pouch, or in a pouch incorporated on an outer side wall of the stoma bag 10. A portable power supply mechanism may allow a patient to power their nutrient recycling device 1 conveniently.

Magnetic Pump Actuator

In one configuration as shown in FIGS. 5A & 5B, the pump actuator 150 is a magnetically driven pump actuator. In at least some embodiments, an impeller is driven by a magnetic coupling between the magnetic pump actuator and the impeller.

In at least some embodiments, the pump actuator 150 comprises a complimentary driving magnet 152 which drives the magnetic piece 110 of the pump 100. In at least some embodiments, the magnetic piece 110 of the pump 100 is attracted to the driving magnet 152 of the pump actuator 150. As the driving magnet 152 of the pump actuator 150 rotates, so does the magnetic piece 110 of the pump 100. In at least some embodiments, as the magnetic piece 110 rotates, the impeller 108 of the pump 100 also rotates to move the digestive contents 6 in the stoma bag 10.

In embodiments using a magnetic coupling between the pump 100 and pump actuator 150 there is no penetration through the bag 10. This pump 100 and pump actuator 150 arrangement may help improve the reliability of the nutrient recycling device 1 and may reduce complexity (especially of disposable parts). The nutrient recycling device 1 may also be attractive to the patient as they will not need to handle the digestive contents 6 to drive the pump 100.

As the patient brings the pump actuator component 150 close to the pump component 100, they will be attracted to each other which makes coupling the two components quick and easy. Detaching the pump actuator 150 is also simple with a magnetic arrangement.

In at least some embodiments, the pump 100 with a magnetic element 110 and a separate corresponding pump actuator 150 provides a clear separation of internal stoma bag components and external components. This configuration may help ensure that the nutrient recycling device 1 is leak-proof. Furthermore, a nutrient recycling device 1 comprising separable internal and external parts may permit disposable parts such as the stoma bag 10 to be easily replaced.

In some configurations, the power of the pump actuator 150 can be controlled. In at least some embodiments, the device 1 comprises a controller to increase or decrease the flow rate of the digestive contents 6. For example, a lower flow rate may be desired for neonates.

Optionally, the nutrient recycling device 1 comprises a flow meter configured to measure the function of the pump 100 and the flow of the digestive contents 6. This may be useful to determine whether the pump needs maintenance.

The nutrient recycling device 1 comprises a timer adapted to show how much time has elapsed since the pump was last use. This may be useful to help determine when the pump 100 should be turned on, especially if the nutrient recycling device 1 is operated manually. This may help prevent excessive bacterial contents accumulating in the bag 10.

Mechanical Pump Actuator

In another configuration as shown in FIG. 5C, the pump actuator 160 is mechanically coupled to the pump. In at least some embodiments, an impeller is driven by a mechanical coupling between the pump actuator 160 and the impeller.

In at least some embodiments, the pump 100 comprises an opening 140 adapted to receive a complimentary key piece 162 to drive the pump.

In at least some embodiments, the pump actuator 160 comprises the complimentary key piece 162.

The pump actuator key piece 162 mechanically engages with the pump opening 140. As the driving key piece 162 of the pump actuator 160 rotates, so does the pump 100. In at least some embodiments, as the impeller 108 of the pump 100 rotates, the digestive contents 6 in the stoma bag 10 is driven towards the second conduit 20.

Manual Automatic Operation

In one configuration, the patient or medical practitioner or caregiver can manually turn on the nutrient recycling device 1 on demand. In at least some embodiments, the device runs continuously or runs from time to time to pump the digestive contents 6. In at least some embodiments, the digestive contents 6 are pumped towards the distal opening 4 of the ileum 2.

The nutrient recycling device 1 in some configurations comprises a switch, button, or can turn on the device by connecting it to a power supply. Optionally, the device 1 can be switched between an on-demand setting, or pre-set automatic settings.

In another configuration, the nutrient recycling device 1 can operate automatically. In at least some embodiments, a controller operates to increase or decrease the flow rate of the digestive contents 6.

In at least some embodiments, the controller can start and stop the operation of the pump 100. In one configuration the controller can be operated manually by a patient or a caregiver.

In another configuration the controller can operate automatically. This may permit, if the patient wants, the digestive contents 6 to be recycled at set intervals. For example, a night-time mode can operate automatically even when the patient is asleep.

A programmable controller may also permit customized delivery of the digestive contents 6 into a patient. For example, for patients with short bowel syndrome, or prior to ileostomy reversal surgery or other gastrointestinal disorders, individualized delivery of digestive contents 6 is in at least some embodiments tailored to each patient to improve absorption of nutrients. The individualized delivery may be automated according to a programmable schedule tailored to each patient's needs.

In at least some embodiments, the pump 100 operates in a forward direction to pump the digestive contents 6 out of the bag. In some configurations, it may be desirable to reverse the pumping direction to clear blockages in the nutrient recycling device 1. In at least some embodiments, the pump operates in a reverse direction to clear blockages in the nutrient recycling device.

In one configuration, the pump 100 operates in a reverse direction from time to time to clear blockages in the nutrient recycling device.

In some configurations, the pump 100 operates in the reverse direction at the beginning of the cycle, and operates in a forward direction for the remainder of the cycle to pump the digestive contents 6 out of the bag 10.

In another configuration, the pump 100 operates in a reverse direction when a sensor detects a predetermined condition to clear blockages. This predetermined condition may indicate that the pump 100 is blocked, partially blocked, or when there is a reduced in flow of digestive contents 6.

In yet another configuration, the pump 100 alternates between a forward direction and a reverse direction to clear blockages in the nutrient recycling device.

In at least some embodiments, the pump 100 in at least some embodiments provides substantively the same flow or pressure in each turn.

In t at least some embodiments, the pump 100 provides substantially the same flow or pressure when operating in a forward direction and the reverse direction.

Optionally, different pump actuators can be used by the patient for different charging requirements. For example, a night-time pump actuator may be used to power the pump 100 at set intervals such as during the night-time. Another pump actuator 150 can be used by the patient to power the pump 100 on demand.

The nutrient recycling device 1 can be set to operate at set intervals. In at least some embodiments, the pump 100 operates every 10 minutes to 8 hours depending on what the patient requires. In at least some embodiments, the nutrient recycling device 1 is set to operate approximately every 30 minutes to 6 hours. Alternatively, the nutrient recycling device 1 operates continuously.

The nutrient recycling device 1 in at least some embodiments operates for approximately 30 seconds to 20 minutes at a time or until the stoma bag 10 is emptied (fully or to a desired level).

Optionally, the nutrient recycling device 1 can be set to operate at a lower flow rate during times when the patient wants the device to be operating quietly, such as when they are sleeping or when they are in a public setting.

Optionally, the pump 100 is constantly connected to a power supply. This may be used in cases where the pump function may need to be automated, or constantly running such as in the case of neonates in the intensive care unit.

Optionally, the power supply can be attached to the side of an incubator or bed.

In some configurations, the pump 100 can operate at a low slow rate to reduce the chance of waking the patient through pump vibrations. A slow rate may also be beneficial for patients who experience sensations of fullness, discomfort or nausea with higher emptying rates.

In at least some embodiments, the digestive contents 6 is recycled often enough to prevent high growth rates of adverse bacteria within the stoma bag 10.

Optionally, the pump 100 is automatically activated after receiving certain outputs from a sensor. For example the pump 100 may be activated when a fluid level sensor, a bag weight sensor or an optical sensor detects when the bag 10 has reached a certain fullness. Alternatively the pump 100 may be activated when a sensor detects a certain amount of bacteria accumulated in the bag reaches a certain level.

Pump Actuator Attachment

The pump actuator 150 is incorporated with the stoma bag 10. In one configuration, the pump actuator 150 is located inside the bag. In another configuration, the pump actuator 150 is attached externally to the bag. Optionally, the pump 100 forms at least part of the bag wall.

In one configuration, the pump actuator 150 can be attached to a side wall of the bag (inside or outside). In at least some embodiments, pump actuator 150 is attached to the outer side wall of the bag.

In one configuration, the pump 100 is located inside the bag 10 and the pump actuator 150 is located external to the bag 10. Thus, the pump actuator 150 is not in contact with the digestive contents 6 and remains clean, while being able to drive the pump 100 from outside the bag 10.

In another configuration, the stoma bag 10 comprises a pouch adapted to store the pump actuator 150. In at least some embodiments, the pouch is incorporated into a side wall of the stoma bag 10. It may be possible for a pump actuator 150 to be attached to the stoma bag 10, such as for patients who operate the pump 100 in an automated mode, such as use overnight. Some patients with high outputs, fistulas, and arthritis, or poor vision may also benefit from a pump actuator 150 attached to the stoma bag 10.

In yet another configuration, the pump actuator 150 is incorporated with the stoma bag 10 by fastening means such as clips, clasps, buckles, Velcro, zip, slide fastener, snap fasteners, magnets or other fasteners known in the art.

Optionally, the pump actuator 150 can be adhered to the side wall of the stoma bag 10 by adhesion methods known in the art.

In another configuration, the stoma bag 10 comprises magnets adapted to attract the pump actuator 150 in the desired location.

Optionally, the pump actuator 150 is incorporated with the pump 100 as shown in FIG. 4C, and it can be powered by a separate power cord. In one configuration, the pump 100 and pump actuator 150 components are external to the stoma bag 10 as shown. Alternatively, the pump 100 and pump actuator 150 components are internal to the stoma bag 10. Optionally, a power cable is provided external to the stoma bag 10.

In at least some embodiments, the pump actuator 150 is located in close proximity to the pump 100.

Peristaltic Pump

In another configuration, the nutrient recycling device 1 comprises a peristaltic pump 200 as shown in FIG. 6. The peristaltic pump 200 comprises a body 201, with a pump inlet 202. In at least some embodiments, the pump inlet 202 is located at or towards the bottom of the stoma bag 10.

In at least some embodiments, the peristaltic pump 200 is located within the stoma bag 10 so the pump is in fluid communication with the digestive contents 6.

Alternatively, the peristaltic pump 200 is located external to the stoma bag 10. Optionally, an external peristaltic pump 200 is connected to the stoma bag 10 by external conduits.

In at least some embodiments, the peristaltic pump 200 comprises a pump conduit 203 located within the pump body 201. In at least some embodiments, digestive contents 6 enter the pump conduit 203 through the pump inlet 202.

In at least some embodiments, the peristaltic pump 200 comprises an impeller 204 to drive the digestive contents 6 from a first end of pump conduit 203 to a second end. In at least some embodiments, the second end of the pump conduit 203 is connected or is continuous with a first conduit 220. In at least some embodiments, the first conduit 220 connects the pump 200 to the distal opening 4 of the ileum 2.

In at least some embodiments, the impeller 204 comprises rollers 205. In at least some embodiments, the rollers 205 are located towards the periphery of the pump. As the impeller 204 rotates, the rollers 205 compress the pump conduit 203 and pumps the digestive contents 6 in the direction of rotation to the outlet of the pump. The rollers 205 are configured to compress the pump conduit 203 to drive the digestive contents through the pump conduit.

Optionally, the impeller 204 is configured to grind up the digestive contents 6 into smaller particles, to reduce the chances of blockages.

Piston Pump

In another configuration, the nutrient recycling device 1 is a piston pump comprising a syringe pump 300 as shown in FIG. 7. The syringe pump 300 comprises a body 301, with a pump inlet 302. In at least some embodiments, the pump inlet 302 is located at or towards the bottom of the stoma bag 10.

In at least some embodiments, the syringe pump 300 is located or partially located external the stoma bag 10 so the patient or medical caregiver can operate a plunger 304 of the syringe.

In at least some embodiments, as the plunger 304 is pulled linearly along the inside of the body 301 to draw and eject digestive contents 6. In at least some embodiments, as the plunger 304 is pulled, digestive contents 6 is drawn into the plunger pump 300 through the inlet 302.

As the plunger 304 is pushed, digestive contents 6 is forced through an outlet 303. In at least some embodiments, as the plunger 304 is pushed, the digestive contents 6 is forced through a first conduit 320. In at least some embodiments, the first conduit 320 connects the syringe pump 300 to the distal opening 4 of the ileum 2. In at least some embodiments, the syringe pump 300 is configured to push the digestive contents 6 to the distal opening 4 of the ileum 2.

In the at least some configuration, the plunger pump 300 comprises one or more one-way valves within a flow channel 313. In at least some embodiments, the one-way valves are adapted to ensure that when the plunger 304 is pulled, digestive contents 6 is drawn into the plunger pump. In at least some embodiments, the one-way valves are also adapted to ensure that when the plunger 304 is pushed, digestive contents 6 are ejected towards the outlet 303.

Valve Pump

In yet another configuration, the nutrient recycling device 1 comprises a valve pump 400 as shown in FIG. 8. The valve pump 400 comprises a pump inlet 402. In at least some embodiments, the pump inlet 402 is located at or towards the bottom of the stoma bag 10. Optionally, the valve pump 402 comprises an inlet conduit 419 to guide the digestive content 6 from within the stoma bag 10 to the inlet 402 of the pump.

In at least some embodiments, the valve pump 400 is located within the stoma bag 10 so the pump is in fluid communication with the digestive contents 6.

In at least some embodiments, the valve pump 400 comprises a first valve 404. Optionally, the valve pump 400 comprises a second valve 405.

In at least some embodiments, a first portion of the conduit 420 connects the valve pump 400 to the distal opening 4 of the ileum 2. The first portion of the conduit 420 is adapted to be compressed to drive the digestive contents towards the distal opening 4. In at least some embodiments, the first portion of the conduit 420 recoils after being compressed to suck further digestive contents 6 into the conduit for the next pump sequence.

A patient can manually do this by compressing the first conduit 420 through the stoma bag 10. The first valve 404 and/or second valve 405 prevents backflow of the digestive contents as the digestive contents are pumped up the first conduit 420.

Optionally, the nutrient recycling device 1 comprises a button or target configured to assist in compressing the first conduit 420.

Optionally, the nutrient recycling device comprises an external component adapted to assist in compressing the first portion of the conduit 420. Alternatively, an automated mechanism can be used to compress the conduit 420 at set intervals.

Optionally the nutrient recycling device 1 is constructed from a kit of parts.

Squeezable Bag

In some configurations, the nutrient recycling device 1 is configured to be pumped by manual manipulation of the bag 10 by the patient, caretaker, and/or medical practitioner as shown in FIGS. 9A-9C. In this configuration, at least a section of the bag 10 is configured to be externally compressed by a patient to pump the digestive contents 6 along a flow pathway 500. The flow pathway 500 in at least some embodiments begins from or near the first bag opening 3, and leads to the distal opening 4 of the gastrointestinal tract.

In at least some embodiments, the pumping of waste is achieved by manual compression of the bag 10, by a patient, to drive the digestive contents 6 in a desired flow pathway as illustrated by arrow 500 in FIG. 9A. The pathway comprises a pathway inlet configured to receive digestive contents 6 from the proximal opening. The pathway also comprises a pathway outlet connected to an outlet conduit 20 at a junction 510. In at least some embodiments, the junction 510 between the pathway outlet and the outlet conduit 20 is located within the bag 10.

In this configuration, the bag 10 itself forms the pump body. In some configurations, the patient uses their hands to compress segments of the bag 10 to drive the digestive contents 6 towards the outlet conduit 20, leading to the distal opening 4 of the ileum 2. In other configurations, the patient may use a compression aid 504 to compress and drive the digestive contents 6 to the outlet conduit 20 (later discussed).

In at least some embodiments, the bag 10 is configured to be manually compressed by a patient to drive the digestive contents 6 along a sealed pathway to or towards the outlet conduit 20 of the nutrient recycling device 1.

A first end of the outlet conduit 20 is in at least some embodiments configured to receive digestive contents 6 from the bag 10. A second end of the outlet conduit 20 is in at least some embodiments connected to the distal opening 4 of the ileum 2 to guide the digestive contents 6 to the distal gastrointestinal tract.

In at least some embodiments, the patient squeezes the bag 10 in a sliding motion to drive the digestive contents 6 to or towards the outlet conduit 20 of the nutrient recycling device 1.

In at least some embodiments, the stoma bag 10 is configured for pumping by manual compression comprises a flow pathway 500 in fluid communication with the first end of the outlet conduit 20. In at least some embodiments, the nutrient recycling device 1 comprises a junction 510 where the flow pathway 500 leads to the outlet conduit 20.

Alternatively, the patient can compress the bag 10 repetitively. In at least some embodiments, each successive compression is located closer towards the outlet conduit 20, to drive the digestive contents 6 towards the outlet conduit 20.

As the patient compresses a segment of the bag 10, the sidewalls of the bag 10 move inwards, and towards each other to form a compression site 503 as shown in FIG. 9A. As the bag 10 is compressed, the volume of the bag reduces at the compression site 503, and an area of high pressure is formed. The digestive contents 6 are driven from the area of high pressure created by the compression of the bag 10 to an area of lower pressure. The area of lower pressure is in at least some embodiments located downstream of the compression 503 closer towards the outlet conduit 20.

In another configuration, the patient can roll up the bottom of the bag 10 to direct digestive contents 6 towards the opening of the outlet conduit 20. As the bottom of the bag 10 is compressed an area of high pressure is created. The digestive contents are 6 driven to move upwards, to a lower pressure area. Optionally, a paddle or rod is attached to the bottom of the bag 10 to assist with rolling of the bag 10 and/or driving the digestive content 6 upwards.

To prevent backflow, the outlet conduit 20 leading to the distal opening 4 in at least some embodiments comprises one or more one way valves to prevent backflow of the digestive contents 6.

The manual compression of the bag 10 by a patient can be a stand-alone pump to drive the digestive contents 6, or used in conjunction with the other pump mechanisms previously described, or other known pumps.

Optionally, in another configuration, the patient can manually manipulate the bag 10 by inverting the bag 10 to allow gravity to drive the digestive contents 6 to or towards the outlet conduit 20, leading to the distal opening 4 of the ileum 2.

Bag Shape

In at least some embodiments, the stoma bag 10 comprises a doughnut-shape. In this configuration, the bag 10 comprises an aperture 507 through the bag 10. In at least some embodiments, the bag 10 comprises a defined sealed pathway around the perimeter of the aperture 507.

This shape partially separates regions of the bag 10 and to define a pathway 500 for the digestive contents 6. In at least some embodiments, the doughnut-shaped bag 10 separates a first region 501 and a second region 502.

The first region 501 of the bag 10 receives the digestive contents 6 from the proximal opening 3 of the ileum 2. In at least some embodiments, the patient drives the digestive contents 6 to a second region 502 of the bag 10. The second region 502 of the bag 10 provides a pathway 500 to or towards the outlet conduit 20.

In at least some embodiments, the aperture 507 provides a convenient place to attach a clip 504 to prevent backflow (discussed later).

In some configurations, the aperture 507 of the bag 10 may be used to allow the patient to easily put their fingers through and grip around a segment of the bag 10 and to compress the bag 10 to drive the digestive contents 6 in the flow pathway 500.

In at least some embodiments, the aperture 5 is positioned near the center horizontally, to separate the first region 501 and a second region 502 substantially evenly.

In at least some embodiments, the aperture 5 is positioned below the stoma 5 (and the first and second opening of the gastrointestinal tract) so that the digestive contents 6 can enter the inside of the bag 10 and be guided into the desired pathway. In at least some embodiments, the aperture 507 is positioned near the stoma opening 5 to allow a large area for collecting digestive contents 6 while providing for separate regions in the bag 10.

In other configurations, where there is not an aperture 507 to separate the first region 501 and the second region 502, opposite internal sidewalls of the bag 10 can be joined together to separate the first region 501 and second region 502 of the bag 10. For example, opposite internal sidewalls of the bag 10 can be plastic welded together to separate regions of the bag 10. In at least some embodiments, opposite internal side walls along a longitudinal axis of the bag are joined together to separate the separate regions of the bag 10.

The doughnut-shaped bag 10 is in at least some embodiments positioned over a stoma 5 of a patient. In at least some embodiments, a top section of the bag 10 is positioned over the stoma 5. The doughnut-shaped bag 10 covering a stoma 5 allows access to the proximal opening 3 and distal opening 4 of the gastrointestinal tract when it is in use, while closing the internal contents 6 of the bag off from the rest of its surroundings.

In yet another configuration, the bag 10 forms a U-shape, as a first end of the bag 10 is connected to the proximal opening 3 of the ileum 2, and a second end of the bag 10 is connected to the distal opening 4 of the ileum 2. A U-shape bag 10, like a doughnut-shaped bag 10 allows the patient to easily grip around segments of the bag 10 to drive the digestive contents 6 in the flow pathway 500.

In some configurations, the bag 10 is a flexible tube which connects the proximal opening 3 of the ileum 2, to the distal opening 4 of the ileum 2. The flexible tube is adapted to be compressed by the patient to drive the digestive contents 6 to or towards the outlet conduit 20. A nutrient recycling device 1 comprising a flexible tube, external to a patient's body, connecting to the proximal opening 3 and the distal opening 4 of the ileum imitates the small intestine 2.

In another configuration, the bag 10 comprises a lower section comprising a smaller width than the upper section of the bag 10. A bag 10 comprising a tapered lower region may be beneficial where the patient compresses the bottom of the bag 10 to pump the digestive contents 6 upwards. A tapered lower region can make squeezing easier for patients, or more efficient as the digestive contents 6 are driven from an area of high pressure in the compressed lower region, to an area of low pressure in an upper region of the bag 10.

The tapered lower region can be a bulb or bladder shape.

Optionally, the tapered lower region of the bag 10 comprises, or is covered by a secondary material such as rubber to make squeezing more efficient. Optionally, the tapered lower region of the bag 10 comprises a textured surface to make squeezing more efficient.

In other configurations, the patient compresses a stoma bag 10 comprising a substantially rectangular, rounded rectangular, or oval shape.

Clip

In at least some embodiments, the nutrient recycling device 1 comprises a clip 504. In at least some embodiments, the clip 504 is externally attached to the bag 10 of the nutrient recycling device 1 as shown in FIG. 9B.

The clip 504 can be used by a patient to compress a segment of the bag 10, forming a compression site 503. The clip 504 in at least some embodiments separates an upstream region and a downstream region of the bag 10, and limits flow from travelling upstream of the clip. In at least some embodiments, the clip 504 limits digestive content 6 travelling back upstream towards the proximal opening 3.

The clip 504 is configured to isolate high pressure areas and desired low pressure areas from each other when the bag 10 is compressed. As the bag 10 is compressed, the clip 504 in at least some embodiments allows the region downstream the clip to be pressurized, while isolating the upstream region. In at least some embodiments, the region upstream of the clip 504 maintains a lower pressure than the downstream region. Isolating the upstream and downstream regions of the clip 504 can limit the risk of detaching the nutrient recycling device 1 from a patient, during compression of the bag 10, due to potential high pressure at the stoma 5 attachment site.

In at least some embodiments, the compression site 503 is formed close to, or at the level the digestive contents 6 rests when it is collected at the bottom of the bag 10.

In at least some embodiments, the clip 504, forms a first end of the pathway 500. In at least some embodiments, the patient manually compresses a segment of the bag 10 downstream the clip 504, towards the outlet conduit 20.

The clip 504 may also be beneficial to assist in directing the digestive contents 6 along the desired flow pathway 500, towards the opening of the outlet conduit 20.

The clip 504 in at least some embodiments prevents back flow of the digestive contents 6, when a segment of the bag 10 is manually compressed. When the bag 10 is compressed, the clip 504 in at least some embodiments prevents or reduces the volume of digestive contents 6 flowing upstream, towards the proximal opening 3. Instead, the digestive contents 6 are limited to flow in the desired flow pathway 500, towards the opening of the outlet conduit 20. In at least some embodiments, as the bag 10 is compressed, the digestive contents 6 are driven from the area of high pressure created by the compression of the bag 10, away from the clip 504, to an area of lower pressure. The area of lower pressure is in at least some embodiments located closer towards the outlet conduit 20.

In at least some embodiments, the clip 504 is removably attached to the bag 10. The clip 504 can be removed once the patient has finished emptying the digestive contents 6 by driving the digestive contents 6 to the outlet conduit 20. This may permit the patient to wear the bag 10 on its own without any attachments.

In the embodiment as shown in FIG. 9B, the clip 504 comprises two adjacent clip legs. In at least some embodiments, the clip legs are movable relative to one another. Each clip leg is configured to be positioned on opposite outer sidewalls of the bag 10. The clip legs are configured to be pressed together to compress a segment of the bag 10, forming a compression site 503.

In at least some embodiments, the clip 504 comprises a securing means 508 configured to secure the two clip legs together. Optional, a first leg of the clip 504 comprises a female portion, and a second leg of the clip 504 comprises a male portion configured to fit together and secure the clip legs together.

Other securing means known in the art such as a drawstring may be used as an alternative to the clip 504.

Alternatively, the clip 504 can be attached to the bag 10 permanently, or semi-permanently. For example, in some configurations, a band which permanently encircles a segment of the bag 10 is used to prevent backflow.

Slider

In some configurations, the clip 504 can be used as a compression aid. In other configurations, an additional clip (not shown) can be used as a compression aid.

A compression aid 504 is in at least some embodiments used by a patient to compress a segment of the bag 10, and drive the digestive contents 6 to or towards the outlet conduit 20

The compression aid 504 is in at least some embodiments slidable, to drive digestive contents 6 towards the outlet conduit 20. In at least some embodiments, the compression aid 504 drives the digestive contents 6 from a first region 501 of the bag 10 towards the second region 502 of the bag 10.

The compression aid 504 may compress the bag 10 and provide generally continuous pressure at the compression site 503. In at least some embodiments, the compression aid 504 applies pressure across an entire width of the pathway 500, urging the bag walls together.

The compression site 503 is in at least some embodiments easily maintained with the compression aid 504, even when it slides along the bag 10 to drive the digestive contents 6 along the flow pathway 500. The compression site 503 in at least some embodiments shifts from a first region 501 towards second region 502 of the bag 10, as the compression aid 504 moves from the first region towards the second region.

The compression aid 504 in at least some embodiments creates an area of high pressure in the bag, driving the digestive contents 6 to an area of lower pressure.

In at least some embodiments, the compression aid 504 also prevents back flow of the digestive contents 6. In at least some embodiments, the compression aid 504 or prevents the digestive contents 6 from flowing upstream of the compression aid 504, back towards the proximal opening 3.

In at least some embodiments, the compression aid 504 is removably attached to the bag 10. The compression aid 504 can be removed once the patient has finished emptying the digestive contents 6 by driving the digestive contents 6 to the outlet conduit 20, and may permit the patient to be able to wear the bag 10 on its own without any attachments.

Alternatively, the compression aid 504 can be attached to the bag 10 permanently, or semi-permanently. For example, in some configurations, the compression aid 504 is a band which permanently encircles a segment of the bag 10.

Funnel

In at least some embodiments, an internal component of the bag 10 provides a pathway 500 towards the outlet conduit 20.

In some configurations, the bag 10 comprises a funnel 505 located inside the bag 10. The internal funnel 505 in at least some embodiments converges towards the outlet conduit 20 configured to direct the digestive contents 6 towards the outlet conduit 20. The funnel 505 in at least some embodiments comprises a wide inlet located towards the bottom of the bag 10 configured to receive the digestive contents 6. In some configurations the inlet of the funnel 505 is the width of the second region 502 of the bag 10. The inlet is located upstream from the outlet of the funnel.

In at least some embodiments, the funnel 505 is located towards the bottom of the bag 10, so that the inlet of the funnel is in fluid communication with the digestive contents 6 even when the bag 10 is only partially filled. This may be useful to limit occurrences of air being pumped through to the outlet conduit 20.

The funnel 505 in at least some embodiments comprises a narrow outlet located at or towards the outlet conduit 20, configured to direct the contents of the bag 10 to or towards the outlet conduit 20. In at least some embodiments, the outlet of the funnel 505 is located downstream of the inlet.

In the configuration as best shown in FIG. 9B, the funnel 505 is connected to the outlet conduit 20 forming a connection point, at the junction 510. In at least some embodiments, the connection point 510 connects the flow pathway 500 to the outlet conduit 20, leading to the distal opening 4 of the ileum 2.

In at least some embodiments, the funnel 505 comprises integrated tubing configured to be connected to the outlet conduit 20 leading to the distal gastrointestinal tract.

In at least some embodiments, the funnel 505 comprises integrated tubing along the narrow region of the funnel. This may provide for a better connection between the funnel 505 and the outlet conduit 20.

In some configurations, the funnel 505 is created at least partially by welding opposing side walls of the bag 10 to form the shape of a funnel, to direct the flow of the digestive contents 6 to or towards the outlet conduit 20.

In other configurations, the funnel 505 is a component formed separate to the side walls of the bag 10. In some configurations, the separate funnel 505 is connected to the internal sidewall of the bag 10. In at least some embodiments, the funnel 505 is plastically welded to the internal sidewall of the bag 10. In other configurations, the funnel 505 is connected to the sidewalls of the bag 100 by other adhesion means known in the art.

Filter

In at least some embodiments, the bag 10 comprises a filter 512 as shown in FIG. 9C configured to separate finer digestive contents 6 from larger particulate matter.

The filter 512 is in at least some embodiments a mesh which separates finer digestive contents 6 from larger particulate matter.

In at least some embodiments, the filter 512 limits digestive content with a diameter larger than the outlet conduit 20 from passing through it.

In at least some embodiments, the filter 512 can help separate the bag 10 into sub-compartments. The digestive contents 6 pass through a first sub-compartment, and only finer particles enter a second sub-compartment, downstream from the first sub-compartment.

The use of a filter 512 can reduce the likelihood of the outlet conduit 20 from being blocked, which may require medical attention or replacement of the component.

Optionally, the larger particulate matter isolated from the digestive contents 6 can be emptied from an opening in the bag 10.

In one configuration, the isolated particulate matter can be emptied from a drainage bag opening 13, in at least some embodiments located at the bottom of the bag 10. In this configuration, patient only has to empty the ruminant larger particulate matter remaining in the bag, while most of the digestive contents 6 are regularly recycled to the distal gastrointestinal tract.

Optionally, the bag 10 comprises an opening located close to the filter 512 to allow filtered digestive contents 6 to be removed from inside of the bag 10. In at least some embodiments, the opening is resalable.

Alternatively, the patient can simply replace the bag 10 as required.

In the one embodiment, the filter 512 is located between the compression site 503 and the funnel 505. In at least some embodiments, the filter 512 is located in the bottom region of the bag 10 where the digestive matter 6 is generally collected. As the digestive contents 6 are driven from a first region 501 of the bag to a second region 502, the filter 512 separates different sized particles of the digestive content 6.

In another embodiment, the filter 512 is located in the upper first region 501 of the bag 10, towards the proximal opening 3. As the digestive contents 6 enter the bag 10 from the proximal opening 3, finer digestive contents 6 fall to the bottom of the bag 10 due to gravity. In at least some embodiments, larger particulate matter remains upstream of the filter 512.

Optionally, the filter 512 is located in the funnel 505. In at least some embodiments, the filter 512 limits larger partially digested particulate matter from entering the narrower section of the funnel, and creating blockages. This may permit a single internal component to be attached to the bag 10 with the dual function of directing digestive content 6 to the outlet conduit 20, while limiting blockages.

This configuration may enable a patient to eat a generally unrestricted diet while still utilizing the nutrient recycling device 1.

As shown in FIG. 9C, in some configurations, the bag 10 comprises a sealed section 506 configured to direct the flow of the digestive contents 6 to the first region 501 of the bag 10. In at least some embodiments, the sealed section 506 is located in the second region 502 of the bag 10. The sealed section 506 seals opposite walls of the bag 10 together to prevent digestive contents 6 from entering the second region 502 from the top end of the bag 10. In some embodiments, an anticlockwise pathway is formed.

In some configurations, the sealed section 506 can be used to create the funnel 505 section during manufacture.

Outlet Conduit Connection

The nutrient recycling device 1 in at least some embodiments comprises an outlet conduit 20 passing outside the bag 10, through the bag opening 11. In at least some embodiments, to allow good patient workflow, the outlet conduit 20 is easily connectable and dis-connectable from a second conduit 30 located in the distal gastrointestinal tract. This may be beneficial, as some patients may want to change the bag 10 of the nutrient recycling device 1 regularly.

To facilitate the replacement of the bag 10, a portion of the outlet conduit 20 extending outside the bag 10 for easy connection with the second conduit 30 which leads to the distal gastrointestinal tract may be useful.

Optionally, the second conduit 30 remains in the distal intestinal tract while the rest of the nutrient recycling device 1 can be removed for replacement, or maintenance.

Benefits

A nutrient recycling device 1 driven by the manual compression of the bag 10 can reduce the likelihood of contamination. A bag 10 configured for manual compression does not communicate with additional components, which reduces the likelihood of leakage.

The pumping action occurs external to a sealed bag 10. As there are no internal components in contact with the digestive contents 6, this eliminates the risk of blockages which may occur with mechanical moving components.

Additionally, a nutrient recycling device 1 with limited components is simple and cheap to manufacture, and expected to be reliable. A nutrient recycling device 1 driven by the manual compression of the bag 10 can be cheaply replaced, and may be beneficial for patients who may want to replace their nutrient recycling device regularly.

The nutrient recycling device 1 is also relatively light, reducing the likelihood of leaks or detachments from the stoma 5.

Furthermore, as the nutrient recycling device 1 driven by the manual compression does not require external energy from batteries, or a pump, there is less risk of device failure. Furthermore, it is generally easier to obtain regulatory approval without mechanical components and therefore relatively easy for medical markets to introduce this configuration of the nutrient recycling device 1.

Further Features

In at least some embodiments, the nutrient recycling device 1 is a partially external component, and is low-impact in nature. The device 1, is in at least some embodiments not significantly more burdensome than wearing a traditional stoma bag.

Patients may find the device 1 attractive as at least some embodiments the device is portable, and may be self-operated and/or managed at home. This is beneficial as some hospital resources can be saved as the patient can manage their own device.

In particular, some patients with low pump actuator control such as with hand arthritis, neurological disorders, or poor vision may find it difficult to manage emptying a stoma bag 10. The nutrient recycling device 1 may help enable these patients' independence, in-between assisted bag changes by a caregiver.

The digestive content recycling capabilities of the device 1 may decrease the need of a patient to regularly empty their stoma bag 10.

Additionally, regular recycling may reduce the risk of stoma bag leaks, which sometimes occur when the bags become overfull.

The nutrient recycling device 1 comprising a stoma bag 10 with an incorporated pump 100 can be easy to operate, and compact and simple to manufacture.

The above describes specific examples/embodiments. The description of such embodiments should only be used to help understand the invention. That is, those skilled in the art should appreciate that the descriptions of embodiments herein are only descriptive and exemplary, and should not be interpreted as limiting the scope of the invention or the claims herein.

Accordingly, it should be noted that several improvements and modifications can be made to the embodiments disclosed herein by those of ordinary skill in the technical art without departing from the principles of the invention, and such that these improvements and modifications fall within the scope thereof. To those skilled in the art to which the invention relates, many changes in construction and widely differing embodiments and applications of the invention will suggest themselves without departing from the scope of the invention as defined in the appended claims.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

What is claimed is:

1. An apparatus comprising:

a nutrient recycling device configured to collect digestive contents from a downstream surgically-created first opening of a gastrointestinal tract and recycle the digestive contents to a second gastrointestinal tract opening, the nutrient recycling device including a flexible bag including a first bag opening adapted to receive digestive contents from the surgically created first opening;

a pathway inlet configured receive digestive contents from the first bag opening;

a first region within the bag configured to receive digestive contents from the pathway inlet;

a second region within the bag configured to receive digestive contents from the first region;

an outlet conduit defining a fluid pathway for digestive contents to flow from the bag to the second gastrointestinal tract opening; and a pathway outlet connected to the outlet conduit at a junction; and wherein the bag defines a doughnut-shape defining an aperture through the bag configured to separate the first region and the second region, and defines a sealed flow pathway within the bag around a perimeter of said aperture; and a pump defining at least a section of the bag configured to be externally compressed by a patient to pump digestive contents along the flow pathway from or near the first bag opening towards the second gastrointestinal tract opening.

2. The apparatus of claim 1, wherein the junction between the pathway outlet and the outlet conduit is located within the bag.

3. The apparatus of claim 1, wherein the device further comprises an internal funnel converging from the pathway outlet towards the outlet conduit.

4. The apparatus of claim 3, wherein the funnel comprises a wide inlet located upstream the outlet conduit, configured to receive the digestive content.

5. The apparatus of claim 3, wherein the funnel is formed at least partially by welding opposing side walls of the bag.

6. The apparatus of claim 3, wherein the funnel is a separate component adhered to side walls of the bag.

7. The apparatus of claim 1, wherein the digestive contents are driven from an area of high pressure created by compression of the bag to an area of lower pressure towards the outlet conduit.

8. The apparatus of claim 7, wherein the aperture is located below the surgically created first opening of the gastrointestinal tract.

9. The apparatus of claim 1, wherein opposite internal side walls along a longitudinal axis of the bag are joined together to separate the first region and the second region.

10. The apparatus of claim 1, wherein the bag defines a U-shape.

11. The apparatus of claim 1, wherein the bag defines a tapered lower region configured to allow the patient to drive the digestive content more efficiently.

12. The apparatus of claim 1, wherein the bag includes a clip configured for compressing a segment of the bag, wherein the clip separates the bag into an upstream region and a downstream region, and is configured to limit flow from travelling upstream of the clip.

13. The apparatus of claim 12, wherein the clip is removably attached to the bag.

14. The apparatus of claim 12, wherein the device comprises a compression aid configured to drive digestive contents to or towards the outlet conduit.

15. The apparatus of claim 14, wherein the compression aid is configured to apply pressure across an entire width of said flow pathway, urging the bag walls together, and to slide along the bag to drive the digestive contents to or towards the outlet conduit.

16. The apparatus of claim 1, wherein the bag comprises a clip configured to fit the aperture through the bag.

17. The apparatus of claim 1, wherein the bag comprises a filter configured to separate fine digestive contents from larger particulate matter.

18. The apparatus of claim 17, wherein the filter is located in the bottom region of the bag where digested matter is generally collected.

19. The apparatus of claim 17, wherein the filter is located in an upper first region of the bag, towards the first gastrointestinal tract opening.

20. The apparatus of claim 1, wherein the bag comprises a sealed section configured to direct the digestive contents to the first region of the bag.

21. A method comprising:

recycling digestive nutrients by collecting digestive contents from a surgically created first opening of a gastrointestinal tract and recycling the digestive contents to a second opening with a nutrient recycling device including a flexible bag including a first bag opening adapted to receive digestive contents from the surgically created first opening;

a pathway inlet configured receive digestive contents from the first bag opening;

a first region within the bag configured to receive digestive contents from the pathway inlet;

a second region within the bag configured to receive digestive contents from the first region;

an outlet conduit defining a fluid pathway for digestive contents to flow from the bag to the second gastrointestinal tract opening; and a pathway outlet connected to the outlet conduit at a junction; and wherein the bag defines a doughnut-shape defining an aperture through the bag configured to separate the first region and the second region, and defines a sealed flow pathway within the bag around a perimeter of said aperture; and a pump defining at least a section of the bag configured to be externally compressed by a patient to pump digestive contents along the flow pathway from or near the first bag opening towards the second gastrointestinal tract opening;

wherein the method further includes positioning the first bag opening over (i) the first opening or (ii) the first opening and the second opening; and compressing the at least a section of the bag and thereby driving the digestive contents along said flow pathway towards the outlet conduit.

22. The method of claim 21, wherein the driving step includes a patient driving said digestive towards the outlet conduit in a sliding motion.

23. The method of claim 21, wherein the driving step includes a patient driving said digestive towards the outlet conduit by compressing the bag repetitively.

24. The method of claim 23, wherein the step of compressing the bag repetitively includes performing successive compressions, wherein each of the successive compressions is located closer towards the outlet conduit than previous of the compressions.

25. The method of claim 21, wherein a clip is externally attached to the bag.

26. The method of claim 25, wherein the clip is removed once the bag has been emptied.

27. The method of claim 21, wherein the outlet conduit is connected to a second conduit located in the second gastrointestinal tract opening.

28. The method of claim 27, wherein the outlet conduit is disconnectable from the second conduit to allow replacement or maintenance of the nutrient recycling device.

* * * * *